US011515008B2

(12) United States Patent
Morrison et al.

(10) Patent No.: US 11,515,008 B2
(45) Date of Patent: Nov. 29, 2022

(54) METHODS AND SYSTEMS FOR DETERMINING PERSONALIZED THERAPIES

(71) Applicant: OMNISEQ, INC., Buffalo, NY (US)

(72) Inventors: Carl Morrison, Fredonia, NY (US); Sarabjot Pabla, Buffalo, NY (US); Jeffrey Conroy, Williamsville, NY (US); Mary Nesline, Buffalo, NY (US); Mark Gardner, Clarence, NY (US); Ji He, North Potomac, MD (US); Sean Glenn, East Amherst, NY (US)

(73) Assignee: OMNISEQ, INC., Buffalo, NY (US)

( * ) Notice: Subject to any disclaimer, the term of this patent is extended or adjusted under 35 U.S.C. 154(b) by 1018 days.

(21) Appl. No.: 15/727,022

(22) Filed: Oct. 6, 2017

(65) Prior Publication Data
US 2018/0107786 A1  Apr. 19, 2018

Related U.S. Application Data

(60) Provisional application No. 62/456,072, filed on Feb. 7, 2017, provisional application No. 62/405,609, filed on Oct. 7, 2016.

(51) Int. Cl.
| | | |
|---|---|---|
| *G16B 40/00* | (2019.01) | |
| *G16B 5/00* | (2019.01) | |
| *G16B 20/00* | (2019.01) | |
| *G01N 33/574* | (2006.01) | |
| *C07K 16/28* | (2006.01) | |
| *C12Q 1/6886* | (2018.01) | |
| *G16B 20/20* | (2019.01) | |
| *G16B 5/20* | (2019.01) | |
| *G16B 20/40* | (2019.01) | |
| *A61K 39/00* | (2006.01) | |
| *G16H 15/00* | (2018.01) | |
| *G16H 50/20* | (2018.01) | |

(52) U.S. Cl.
CPC .......... *G16B 40/00* (2019.02); *C07K 16/2818* (2013.01); *C12Q 1/6886* (2013.01); *G01N 33/574* (2013.01); *G01N 33/57484* (2013.01); *G16B 5/00* (2019.02); *G16B 5/20* (2019.02); *G16B 20/00* (2019.02); *G16B 20/20* (2019.02); *G16B 20/40* (2019.02); *A61K 2039/505* (2013.01); *A61K 2039/55* (2013.01); *C12Q 2600/156* (2013.01); *G16H 15/00* (2018.01); *G16H 50/20* (2018.01)

(58) Field of Classification Search
CPC .......... G16B 40/00; G16B 5/00; G16B 20/20; G16B 5/20; G16B 20/00; G16B 20/40; C07K 16/2818; C12Q 1/6886; G01N 33/574; G01N 33/57484
See application file for complete search history.

(56) References Cited

FOREIGN PATENT DOCUMENTS

| WO | 2016081947 A2 | 5/2016 |
| WO | 2016/094377 | 6/2016 |
| WO | 2016/100975 | 6/2016 |

OTHER PUBLICATIONS

International Search Report Form PCT/ISA/220, International Application No. PCT/US2017/055545, pp. 1-25, dated Feb. 12, 2018.
Invitation to Pay Additional Fees PCT/ISA/220, International Application No. PCT/US2017/055545, pp. 1-20, dated Dec. 19, 2017.
Jonathan E. Rosenberg, et al., Atezolizumab in patients with locally advanced and metastatic urothelial carcinoma who have progressed following treatment with platinum-based chemotherapy: a single-arm, multicenter, phase 2 trial, www.thelancet.com, vol. 387, May 7, 2016, pp. 1-12, published online Lancet 2016; 387:1909-20.
Eric Tran et al., Immunogenicity of somatic mutations in human gastrointestinal cancers, downloaded from http://science.sciencemag.org/, Science 350 (6266), 1387-1390, published online Oct. 29, 2015, pp. 1-5.
Rosenberg, Je, et al., supplement to Atezolizumab in patients with locally advanced metastatic urothelial carcinoma who have progressed following treatment with platinum-based chemotherapy:a single-arm multicentre, phase 2 trial, The Lancet, published online Mar. 4, 2016, pp. 1-25.
Eliezer M. Van Allen et al, Genomic correlates of response to CTLA-4 blockade in metastatic melanoma, sciencemag.org, Oct. 9, 2015, vol. 350 issue 6257, pp. 1-6, published online Sep. 10, 2015.
Naiyer A. Rizvi et al, Mutational landscape determines sensitivity to PD-1 blockade in non-small cell lunch cancer, sciencemag.com, Apr. 3, 2015, vol. 348, issue 6230, pp. 1-6, http://science.sciencemag.org/content/348/6230/124.
Naiyer A. Rizvi et al, Supplementary Materials for Mutational landscape determines sensitivity to PD-1 blockade in no small cell lung cancer, published Mar. 12, 2015 on Science express, www.sciencemag.org/cgi/content/full/science.aaa1348/DCI, pp. 1-31.
Kazuhiko Shien et al, Predictive biomarkers of response to PD-1/PD-L1 immune checkpoint inhibitors in non-small cell lunch cancer, Lung Cancer, Sep. 2016, vol. 99, published online Jun. 21, 2016, pp. 1-7, http://www.lungcancerjournal.info/article/S0169-5002(16)30374-9/fulltext.

(Continued)

*Primary Examiner* — Jerry Lin
(74) *Attorney, Agent, or Firm* — Bond, Schoeneck & King, PLLC

(57) ABSTRACT

A method for generating an immune score, the method comprising the steps of: (i) determining a qualitative and/or quantitative assessment of tumor infiltrating lymphocytes in a sample; (ii) determining a qualitative and/or quantitative assessment of T-cell receptor signaling in the sample; (iii) determining a qualitative and/or quantitative assessment of mutation burden in the sample; (iv) generating, using a predictive algorithm, an immune score based on the determined qualitative and/or quantitative assessment of tumor infiltrating lymphocytes, the determined qualitative and/or quantitative assessment of T-cell receptor signaling, and the determined qualitative and/or quantitative assessment of mutation burden.

19 Claims, 6 Drawing Sheets

(56) References Cited

OTHER PUBLICATIONS

International Preliminary Report on Patentability, International Application No. PCT/US2017/055545, dated Apr. 9, 2019, pp. 1-16.
Japanese Office Action, Japanese Application No. 2019-518486, dated Nov. 24, 2021, pp. 1-6.
Japanese Office Action, Japanese Application No. 2019-518486, dated Jul. 5, 2022, pp. 1-14, with pp. 8-14 being a translation.

| Model | 28 Cpd | 8 Cpd | Immune Function | BRA Trial Prediction |
|---|---|---|---|---|
| Predicted Responder | 23 (26.4%) | 37 (42.5%) | 18 (20.7%) | 26 (29.9%) |
| PPV (Response Rate in Predicted Responders) | 22/23 (95.7%) | 27/37 (73.0%) | 13/18 (72.2%) | 25/26 (96.2%) |
| Predicted Indeterminate | 21 (24.1%) | - | 21 (24.1%) | - |
| Response Rate in Predicted Indeterminate | 5/21 (23.8%) | - | 11/21 (52.4%) | - |
| Predicted Nonresponder | 43 (49.4%) | 50 (57.5%) | 48 (55.2%) | 61 (70.1%) |
| NPV (Nonresponse Rate in Predicted Nonresponders) | 39/43 (90.7%) | 46/50 (92.0%) | 41/48 (85.4%) | 55/61 (90.2%) |

FIG. 9

METHODS AND SYSTEMS FOR DETERMINING PERSONALIZED THERAPIES

CROSS-REFERENCE TO RELATED APPLICATIONS

This application claims priority to U.S. Provisional Patent Application Nos. 62/405,609, filed Oct. 7, 2016 and entitled "Methods and Systems for Determining Personalized Therapies," and 62/456,072, filed Feb. 7, 2017 and entitled "Methods and Systems for Determining Personalized Therapies," the entireties of which are hereby incorporated by reference.

FIELD OF THE INVENTION

The present disclosure is directed generally to methods and systems for generating tumor treatment recommendations.

BACKGROUND

In melanoma and non-small cell lung cancer (NSCLC) patients, a high proportion of somatic mutations—the so-called "mutational burden" (MuB)—as well as elevated intratumoral expression of checkpoint blockades, including the immunosuppressive molecule CD274 (best known as programmed death-ligand 1 protein (PD-L1)), that have been shown to correlate with improved clinical responses to immune checkpoint blocker (ICB)-based immunotherapies. However, predicting the response of patients with other malignancies to immunotherapies—and perhaps in combination of immunotherapy with other targets for immune checkpoint blockade—requires a more profound deconvolution of the immunological tumor microenvironment. Similarly, an in-depth characterization of the immunological configuration of malignancies may be necessary to assist clinical decision making, especially for patients that fail standard ICB-based immunotherapy.

For example, therapeutic antibodies targeting immune checkpoint molecules have been approved by the FDA for the treatment of several types of cancer. However, evaluation of the tumor checkpoint blockade is limited to FDA-approved IHC assays measuring programmed death-ligand 1 (PD-L1) protein status, which is subjective and not analytically robust. As the number of antibodies targeting immune checkpoints expands, assays that can evaluate additional biomarkers in tumor specimens are needed to accurately predict patient response to these drugs.

Accordingly, there is a need for assays capable of characterizing an immunological tumor microenvironment as a guide for therapeutic decisions.

SUMMARY OF THE INVENTION

The present disclosure is directed to inventive methods for determining the presence or absence of cancer cell sensitivity to one or more personalized oncology therapies.

According to one aspect of the invention is a method for generating an immune score, the method comprising the steps of: (i) determining a qualitative and/or quantitative assessment of tumor infiltrating lymphocytes in a sample; (ii) determining a qualitative and/or quantitative assessment of T-cell receptor signaling in the sample; (iii) determining a qualitative and/or quantitative assessment of mutational burden in the sample; and (iv) generating, using a predictive algorithm, an immune score based on the determined qualitative and/or quantitative assessment of tumor infiltrating lymphocytes, the determined qualitative and/or quantitative assessment of T-cell receptor signaling, and the determined qualitative and/or quantitative assessment of mutation burden.

According to an embodiment, the method further includes the step of determining, based on the immune score, one or more possible treatment therapies.

According to an embodiment, the predictive algorithm is trained and updated using machine learning.

According to one aspect of the invention is a method for analyzing a tumor, the method comprising the steps of: (i) determining a qualitative and/or quantitative assessment of tumor infiltrating lymphocytes in a sample; (ii) determining a qualitative and/or quantitative assessment of T-cell receptor signaling in the sample; (iii) determining a qualitative and/or quantitative assessment of mutational burden in the sample; and (iv) classifying, based on the determined qualitative and/or quantitative assessment of tumor infiltrating lymphocytes, the determined qualitative and/or quantitative assessment of T-cell receptor signaling, and the determined qualitative and/or quantitative assessment of mutational burden, the sample as a responder to a therapy or a non-responder to a therapy.

According to an embodiment, the method further includes the step of determining a response of the tumor, based on the determined classification, to one or more possible treatment therapies.

According to an embodiment, the sample is classified as an indeterminate responder to therapy. According to an embodiment, a sample classified as a non-responder to therapy and non-responder to therapy may be further classified as being at risk for hyper-progression of cancer.

According to an embodiment, the method further includes the step of correlating the determined classification of the sample with a second classification.

According to an embodiment, the method further includes the step of determining a response of the tumor, based on the correlation, to one or more possible treatment therapies.

According to an embodiment, the method further includes the step of determining immunohistochemistry data for the sample, wherein said classifying step is further based on the determined immunohistochemistry data.

According to another aspect is a method for analyzing a tumor, the method comprising the steps of: (i) determining a quantitative assessment of an expression level of at least four genes in a sample; (ii) classifying, if the determined quantitative assessment of an expression level of the first of the four genes exceeds a predetermined threshold, the sample as a responder to a therapy, or proceeding to the next step if the determined quantitative assessment of the expression level of the first of the four genes does not exceed the predetermined threshold; (iii) classifying, if the determined quantitative assessment of an expression level of the second of the four genes is greater than a predetermined threshold, the sample as a non-responder to a therapy, or proceeding to the next step if the determined quantitative assessment of the expression level of the second of the four genes does exceed the predetermined threshold; (iv) classifying, if the determined quantitative assessment of an expression level of the third of the four genes exceeds a predetermined threshold, the sample as a responder to a therapy, or proceeding to the next step if the determined quantitative assessment of the expression level of the third of the four genes does exceed the predetermined threshold; and (v) classifying, if the determined quantitative assessment of an expression level of the fourth of the four genes exceeds a predetermined threshold, the sample as a non-responder to a therapy, or classifying, if the determined quantitative assessment of the expression level of the fourth of the four genes does exceed the predetermined threshold, the sample as a responder to a therapy.

According to another aspect is a method for analyzing a tumor, the method comprising the steps of: (i) determining a qualitative and/or quantitative assessment of a plurality of genes related to immune cell infiltration in a sample; (ii) determining a qualitative and/or quantitative assessment of a plurality of genes related to T-cell activation in the sample; (iii) determining a qualitative and/or quantitative assessment of a plurality of genes related to cytokine signaling in the sample; (iv) determining a qualitative and/or quantitative assessment of a plurality of genes related to immune response regulation in the sample; (v) normalizing each of the determined qualitative and/or quantitative assessments; (vi) if the normalized qualitative and/or quantitative assessment of immune cell infiltration exceeds a predetermined threshold, proceeding to an analysis of the normalized qualitative and/or quantitative assessment of T-cell activation in the sample, wherein the sample is classified as a responder if the normalized qualitative and/or quantitative assessment of T-cell activation exceeds a predetermined threshold, and wherein the sample is classified as a non-responder if the normalized qualitative and/or quantitative assessment of T-cell activation does not exceed the predetermined threshold; (vii) proceeding, if the normalized qualitative and/or quantitative assessment of immune cell infiltration falls below the predetermined threshold, to the next step; (viii) classifying, if the normalized qualitative and/or quantitative assessment of immune regulation response exceeds a predetermined threshold, the sample as an indeterminate responder, or proceeding, if the normalized qualitative and/or quantitative assessment of immune regulation response does not exceed the predetermined threshold, to the next step; and (ix) classifying, if the normalized qualitative and/or quantitative assessment of cytokine signaling exceeds a predetermined threshold, the sample as an indeterminate responder, or classifying, if the normalized qualitative and/or quantitative assessment of cytokine signaling does not exceed the predetermined threshold, the sample as a non-responder.

According to another aspect is a method for providing a comprehensive immune profiling clinical report to a patient's clinician, the method comprising the steps of: (i) obtaining one or more samples from a tumor of the patient; (ii) generating, from the one or more samples, RNA sequencing data comprising information about expression of a plurality of tumor-infiltrating lymphocyte proteins and a plurality of T-cell receptor signaling proteins; (iii) generating, from the one or more samples, DNA sequencing data comprising mutational burden information about a plurality of genes; (iv) generating, from the one or more samples, immunohistochemistry data and fluorescent in situ hybridization (FISH) data to measure, among other proteins, PD-L1 protein expression and copy number gain and patterns of tumor infiltrating lymphocyte protein expression for CD3 and CD8; (v) calculating, from the RNA sequencing data, the DNA sequencing data, and the immunohistochemistry and FISH data, a likelihood of the patient's tumor to respond to a plurality of possible treatments; and (vii) providing a comprehensive immune profiling clinical report to the patient's clinician, the report comprising the calculated likelihoods of the patient's tumor to respond to the plurality of possible treatments.

These and other aspects of the invention will be apparent from the embodiments described below.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 9 is a table of overall results from four different models for determining cancer cell sensitivity to one or more personalized oncology therapies, in accordance with an embodiment.

DETAILED DESCRIPTION

Figure 1:
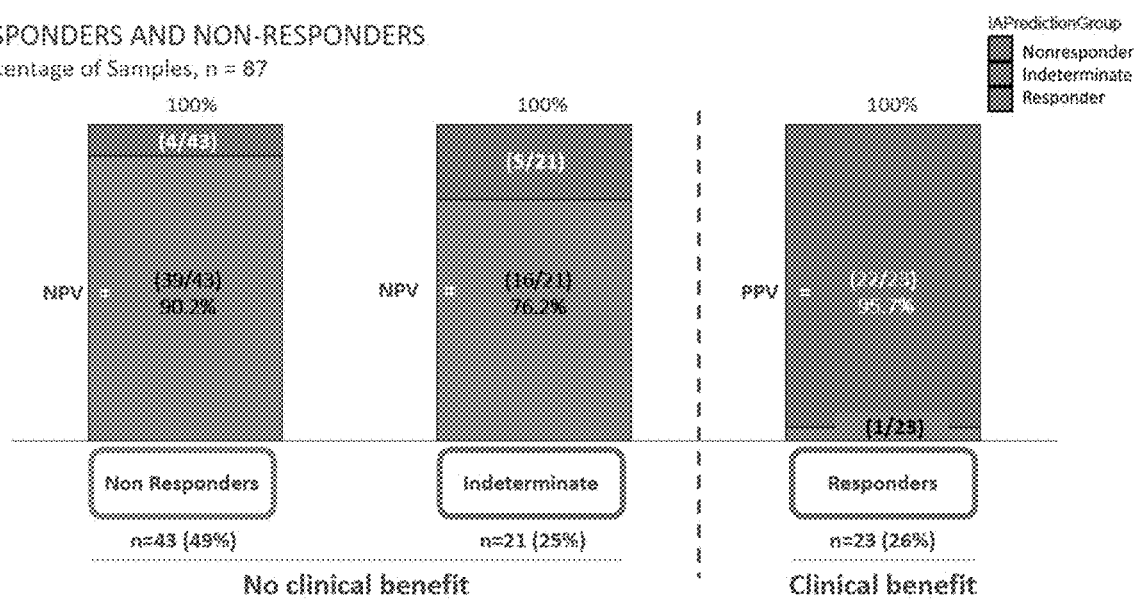
FIG. 1 is a graph of results for a 54 gene model using a panel of retrospective samples for training, in accordance with an embodiment.

The present disclosure is directed to embodiments of a method and system for determining cancer cell sensitivity to one or more personalized oncology therapies.

According to one embodiment, the disclosure is directed to methods for applying a Multi-Analyte Assay with Algorithm Analyses (MAAA) approach to predict therapeutic efficacy. Immune Advance (IA) is a next generation sequencing (NGS) assay designed to provide information about tumor infiltrating lymphocytes (TILs), mutation burden (MuB), T-cell receptor signaling (TCRS), immune-related drug target scores (IRDTSs), and overall immune activation status (i.e., Immune Score). The evaluation of TILs focuses on CD8+ T-cells, but does provide additional information about other subsets of T-cells and related immune effector cells such as B-cells and macrophages. The evaluation of MuB is designed to provide information about the overall number of somatic mutations in a tumor (high versus low), and with no intent to report on specific mutations at the gene level. TCRS, or the signaling of T-cells with both neoplastic cells and other immune-related cells, utilizes expression information from genes representing both receptors and ligands in the interaction of these various cell types. IRDTSs are a set of genes that are the direct targets of one or more immunomodulatory agents, such as CTLA4 and ipilimumab. The Immune Score (IS) utilizes information from TILs, MuB, and TCRS in the context of a reference database of prior clinical outcomes for patients treated with one or more checkpoint inhibitors (CPIs) to provide an assessment of activation of the immune state of the tumor tested.

Immune Advance (IA) is a next generation sequencing assay that uses RNA-Seq to evaluate the mRNA expression of numerous immune related (IR) genes and multiple expression control genes, and DNA-Seq to evaluate mutational burden in a 1.5 Mb targeted capture. The RNA-Seq component validates the expression of the most clinically important genes, and the DNA-Seq component reports a count on non-synonymous mutations with no reference to the specific genes involved. A representative table of 767 genes that, for example, may be utilized in one or more of the RNA-Seq, DNA-Seq, and mutation burden analyses is provided herein as Table 2.

The RNA-Seq component of IA interrogates numerous genes that at the highest level represent more than 40 unique gene functions. IA is focused on the most clinically important genes, of which many are directly related to T-cell receptor signaling (TCRS) and several others for classifying tumor infiltrating lymphocytes (TILs). In the clinical validation portion of IA for all identified clinically important genes, the RNA-Seq data for multiple formalin-fixed, paraffin-embedded (FFPE) specimens is compared to results for custom TaqMan assays, as well as publicly available information for the same set of samples for whole transcriptome analysis via the Cancer Genome Atlas project (TCGA).

Genes related to TCRS may be expressed on immune infiltrating cells or neoplastic cells and are typically classified as pairs of a receptor and associated ligand. For all genes classified in IA as related to TCRS, either the ligand or the receptor is expressed by one or more subsets of T-cells. The current approach to this list of TCRS genes is to divide them into either co-stimulatory or co-inhibitory T-cell function, or checkpoint pathway. Genes related to TCRS can be further divided into those that are the direct target of one or more checkpoint inhibitor drugs versus those that are not. Direct targets of checkpoint inhibitor drugs may be either the receptor or ligand, but not both simultaneously. An example of a checkpoint inhibitor drug and target is ipilimumab and the receptor CTLA-4 that is expressed on activated T-cells.

Genes related to TILs encompass a wide variety of infiltrating immune cells and IA has adopted an existing classification and associated gene expression markers. Classically, an "immunoscore" has been reported as a prognostic marker in multiple tumor types using three (3) or fewer markers of TILs. IA utilizes many more than three genes related to TILs to stratify patients for response to CPIs.

The DNA-Seq component of IA is, for example, a 1.5 Mb AmpliSeq capture of many different cancer-related genes. For IA specific mutations may not be reported, but rather the number of non-synonymous mutations may be reported. The output of the DNA-Seq component of IA, therefore, is an assessment of mutational burden.

Drug-target gene expression analysis is focused on each gene targeted by one or more checkpoint inhibitor drugs, and categorizes each result based upon pre-specified thresholds as High, Intermediate or Moderate, or Low association for the specified drug target. The high, intermediate/moderate, or low association for each drug target is more than a simple evaluation of reads per million for a target gene and encompasses upstream and downstream effectors for that target gene. For example, the primary function of CTLA-4 signaling is to down-regulate T-cell activation by countering the co-stimulatory signal delivered by a second receptor, CD28. Both CTLA-4 and CD28 share the same ligands, CD80 (also known as B7.1) and CD86 (also known as B7.2). CTLA-4 has a higher affinity for both of these ligands than CD28 for ligand binding resulting in an overall co-inhibition signal when expressed at equivalent levels. Clinically, this is countered by administering the CTLA-4 checkpoint inhibitor ipilimumab.

TIL analysis is focused on a semi-quantitative assessment and/or quantitative assessment of TIL(s) and a qualitative and/or quantitative assessment of additional subsets of immune effector cells. In the first instance, tumor infiltrating lymphocytes (TIL) are reported as number of CD3+ and CD8+ transcripts expressed (reads). To aid in the interpretation of the expression level of TIL(s), a direct immunohistochemical comparison is performed for CD3 and CD8 using an Aperio image analysis platform. In the second instance, additional qualitative and/or quantitative markers of Tiic(s) such as FOXP3 for T-regulatory cells, CD163 and CD68 for macrophages, ICOS and CD28 for T-helper cells, and several other markers of subsets of immune cells are categorized for each as a relative expression result based upon pre-specified transcript read thresholds as High, Intermediate, or Low. In contrast to drug-target evaluation the analysis for additional various markers of Tiic(s) is simpler and reflects a ranking to prior observed values.

Mutational burden analysis is focused on number of non-synonymous mutations equivalent to exome sequencing. Results of the 1.5 Mb targeted capture sequence are provided in the context of exome sequencing in the validation of the DNA-Seq component of IA. These results are provided as a High, Intermediate, or Low mutational burden. A mutation burden greater than the equivalent of 200 exomic non-synonymous mutations is reported as high, less than 200 and 150 or greater as intermediate, and less than 150 as low. The cut-offs are arbitrary and reflect a summary of what has been reported in the literature in regard to clinical response to one or more checkpoint inhibitors. Accordingly, many other thresholds are possible.

To summarize the results of drug-target gene expression, immune cell infiltration, and mutation burden, IA provides a single immune score ("Immune Score") on a scale of 0-100 for the overall assessment of immune activation. The IS represents a single patient result that was tested for clinical utility in this validation.

According to another embodiment, the disclosure is directed to methods and systems for generating tumor treatment recommendations using at least three unique models or approaches, independently developed, that can be utilized for comparative purposes and optionally for Bayesian modeling. The multiple models address both a machine learning approach as well as a biological approach to tumor treatment. According to an embodiment, the at least three models will provide a similar response to checkpoint inhibitors, and a Bayesian average model can be utilized to represent the best fit.

The first model, referred to as the 54 gene model and discussed in greater detail below, is a polynomial machine learning regression model. According to an embodiment, the 54 gene model or approach uses 11 genes representing TILs and 43 genes for TCRS combined with MuB for prediction, although other genes and combinations are possible.

The second model, referred to as the 4 gene model and discussed in greater detail below, represents a biological approach at the gene level. According to an embodiment, the 4 gene model or approach utilizes a decision tree model to select the best minimal set of TILs or T-cell activation genes for prediction.

The third model, referred to as the immune function model or the gene functional group model and discussed in greater detail below, represents a biological approach at the functional level. According to one embodiment, this model or approach utilizes 13 genes representing immune cell infiltration, 23 genes for T-cell activation, 10 genes for cytokine signaling, and 8 genes for immune response regulation, although other embodiments are possible.

The fourth model, which is optional, is referred to as the primary immune marker model or approach. The primary immune marker model or approach analyzes one or more immune markers. According to an embodiment, the primary immune marker model or approach analyzes PD-L1 protein expression and/or tumor infiltrating lymphocyte (TIL) expression (including but not limited to CD3 and/or CD8) using immunohistochemistry. According to another embodiment, the primary immune marker model or approach analyzes PD-L1 and/or PD-L2 copy number gain utilizing fluorescent in situ hybridization (FISH) methodology.

According to another embodiment, the method may also optionally utilize PCR analysis or any other methodology to analyze microsatellite instability (MSI), among other possible factors.

Each of the two approaches is described in greater detail below.

Approach #1—The IA Multi-Analyte Assay with Algorithmic Analysis (MAAA)

According to a first approach to deriving a personalized oncology therapy, a multi-factor analysis referred to as Immune Advance (IA) provides a qualitative and/or quantitative assessment of tumor infiltrating lymphocytes (TILs), mutation burden (MuB), and T-cell receptor signaling (TCRS). The three values are used to derive an overall score, referred to as an Immune Score, which is a predictor of the tumor's response to one or more checkpoint inhibitors (CPIs). As just one example, the Immune Score can be reported on a scale of 1-100 and can be grouped as three clinically relevant groups such as high, indeterminate, or low overall response rate to CPIs, among many other possible reporting mechanisms.

IA utilizes a unique algorithmic analysis to provide a qualitative and/or quantitative assessment of tumor infiltrating lymphocytes (TILs), mutation burden (MuB), and T-cell receptor signaling (TCRS). These three values are then used to derive an overall Immune Score. All of these analyses utilize a reference database of prior IA results developed through this validation for future evaluations. This reference database will be updated, for example, on a quarterly basis as prior clinical results are added to the existing results. This update to the reference database will not impact any clinical results prior to the time of the update. Evaluation of TILs, MuB, and TCRS are independent of any known clinical outcomes, but are dependent on the observed values for these parameters in the reference database of prior IA results. In comparison, the Immune Score requires utilization of clinical outcomes in the reference database regarding response to current FDA-approved checkpoint inhibitors (CPIs).

The approach for the IA analysis was developed by first analyzing a group of co-expressed TCRS genes discovered using RNA-seq data from a cohort of specimens. The concept of using TILs and MuB was added to the assessment based upon information provided in the peer-reviewed literature pertaining to response to CPIs as well as prognostic outcomes in various tumor types. Based upon the peer-reviewed literature and analysis of the RNA-seq data from the RPCI TCGA cohort, several genes may be utilized for TIL evaluation. This approach shows that TILs and TCRS are highly associated and co-expressed, while MuB has some but a lesser concordance with these two parameters.

The final approach for the IA analysis was to develop mathematical formulas (i.e., algorithms) that could be used for evaluation of TILs, MuB, TCRS, and IAS in the context of patient stratification of response to CPIs. The endpoint in this analysis was to normalize each of these parameters to a score of 100 to provide a numerical reference of results. The algorithm utilizes 3 different analyses, or steps, in a unique order to derive the final patient stratification for response to CPIs.

Step 1 in the algorithmic analysis is based upon the ranking, or Score, of the observed test result to the reference database for TILs, MuB, and TCRS. For purposes of reporting patient results the TCRS Score is an intermediate value that is not reported while the TILs Score and MuB Score are reported values. The mathematical equation used for this ranking, or Score, is as listed below:

TIL Score means the number of reference samples that have less than or equal to the normalized log 2 reads per million of the average of the TIL-identified genes to the test sample/total number of reference samples*100 and rounded to the closest integer.

TCRS Score means the number of reference samples that have less than or equal to the normalized log 2 reads per million of the average of the TCRS-identified genes to the test sample/total number of reference samples*100 and rounded to the closest integer.

MuB Score means the number of reference samples that have less than or equal to the number of somatic mutations to the test sample/total number of reference samples*100 and rounded to the closest integer.

Step 2 in the algorithmic analysis, the Scores for TILs, MuB, and TCRS are combined into a single value, i.e. Immune Activated Weighted Score (IAWS), using a weighted value for each of these parameters. The mathematical equation used for this Immune Weighted Score (IWS) is as follows:

IWS Score=(TILs Score×weighted value for TILs)+(MuB Score×weighted value for MuB)+(TCRS Score×weighted value for TCRS) and rounded to the closest integer.

The weighted values for TILs, MuB and TCRS may be based, for example, on a machine-learning approach that trains a classifier to produce the optimal IWS (see Step 3) for known therapeutic responders versus non-responders in the reference dataset. This classifier functions such that the IWS of the two classes will be best distinguished, and that weighted value of TILs+weighted value of MuB+weighted value of TCR=1.0. Within the ranked IWS of the reference dataset with responder/nonresponder indications, two thresholds are further determined for calling High/Low scores, so that all reference samples above the high threshold will have >=95% PPV in predicting responders and below the low threshold will have >=95% NPV in predicting nonresponders.

Optional Step 3 in the algorithmic analysis involves transforming the IWS into an Immune Score (IS) based upon the ranking, or Score, of the observed test IWS result to the reference database. For purposes of reporting patient results, the IWS is an intermediate value that is not reported while the IS is a reported value. The mathematical equation used for this ranking, or Score, is as listed below:

IS=(Number of samples in the reference dataset that have less than or equal to the IWS score of the test sample)/total number of reference samples*100 and rounded to the closest integer While the IA algorithm does not change, the reference database of patient responses to CPIs will continue to expand with future clinical testing and follow-up of patient responses. Once a score is assigned to one of the qualitative and/or quantitative assessments for TILs, MuB, TCRS, IWS, or IS that value will not change with future additions to the reference database.

Approach #2—The Integration of Three or More Models

According to a second approach to deriving a personalized oncology therapy, three independent models—the 54 gene model, the 4 gene model, and the immune function model—are utilized individually or in one or more possible combinations. For example, two or more of the three models may be utilized for comparative purposes, and/or may be used for Bayesian or other types of modeling. Each of the three models provide a prediction of the tumor's response to one or more checkpoint inhibitors, and advanced comparative and modeling techniques can provide an average or overall prediction using output from two or more of the three models.

According to the second approach to deriving a personalized oncology therapy, three independent models—the 54 gene model, the 4 gene model, and the immune function model—are utilized individually or in one or more possible combinations. The first model, referred to as the 54 gene model, is a polynomial machine learning regression model that uses 11 genes representing TILs and 43 genes for TCRS combined with MuB for prediction. The second model, referred to as the 4 gene model, represents a biological approach at the gene level and utilizes a decision tree model to select the best minimal set of TILs or T-cell activation genes for prediction. The third model, referred to as the immune function model, represents a biological approach at the functional level and utilizes 13 genes representing immune cell infiltration, 23 genes for T-cell activation, 10 genes for cytokine signaling, and 8 genes for immune response regulation. As described below, the three models can be utilized independently and/or in collaboration to generate or derive a personalized oncology therapy.

According to a further embodiment of the second approach, a fourth model called the primary immune marker model or approach is also utilized. The fourth model analyzes one or more immune markers using immunohistochemistry as described or otherwise envisioned herein.

Model #1—The 54 Gene Model

According to an embodiment, the 54 gene model is a polynomial machine learning regression model that uses 11 genes representing TILs and 43 genes for TCRS combined with MuB for prediction, although other gene combinations are possible.

The 54 gene model was derived by benchmarking different combinations of training and testing data sizes based on a plurality of retrospective samples where the treatment method and tumor response were known. For a training size of N samples, 20,000 iterations of trainings were carried out, each using randomly-drawn N samples and evaluating the performance of the classifier using the rest ((Total # of retrospective samples)−N) testing samples.

The overall performance of the classifier for N-training-sample was calculated from the mean of the 20,000 benchmarks. From an internal benchmark, it was observed that the classifier's ROC/AUC performance converges once N reaches ~50% of the total initial retrospective population.

The published performance metrics (ROC plot, AUC score, PPV and NPV etc.) is calculated out of a more explicit leave-one-out test, i.e. with 87 iterations of unique N=86 tests, each iteration using 86 samples for training while leaving one unique sample for testing purpose. The final prediction model for future testing purpose however used all retrospective samples for training, which in one experimental study was a total of 87 samples.

Referring to FIG. 1, in one embodiment, is a graph of results for the 54 gene model using a panel of retrospective samples for training. As shown in the graph, the results have a positive predictive value (PPV) of 96% for 26% of the population, a negative predictive value (NPV) of 90% for 49% of the population, and an indeterminate group representing 25% of the population.

According to one embodiment, not shown in FIG. 1, the 54 gene model can be determined or designed to classify tumors as being a responder, indeterminate responder, or non-responder to a therapy, and can also be determined or designed to predict the risk of hyper-progression of cancer. For example, the 54 gene model can be determined or designed to identify a subset of non-responders that have a risk of hyper-progressive disease. The risk of hyper-progressive disease may be qualitative and/or quantitative.

According to an embodiment, the 54 gene model utilizes expression information for 54 different genes, and/or mutational burden as the sum of mutation counts in 409 genes. Table 1 includes a representative list of genes for which expression information can be utilized in the 54 gene model. However, many other genes are possible for expression analysis in this model, including but not limited to the genes identified in Table 2.

TABLE 1

Genes Utilized for an Embodiment of the 54 Gene Model

| TILs Genes (11) | TCRS Genes (43) | | | |
|---|---|---|---|---|
| CD163 | ADORA2A | CD40LG | TIM3 | PD-L2 |
| CD2 | BTLA | CD80 (B7-1) | ICOS | STAT1 |
| CD3D | VISTA (B7-H5) | CD86 (B7-2) | ICOSLG | TBX21 |
| CD3E | CCL2 | CSF1R | IDO1 | TGFB1 |
| CD3G | CCR2 | CTLA4 | IFNG | TNF |
| CD4 | SLAMF4 | CXCL10 | IL10 | TNFRSF14 |
| CD68 | CD27 (TNFRSF27) | CXCR6 | IL1B | GITR |
| CD8A | PD-L1 | DDX58 | KLRD1 | OX40 |
| CD8B | CD28 | ENTPD1 | LAG3 | CD137 |
| FOXP3 | CD38 | GATA3 | MX1 | OX-40L |
| CD20 | CD40 | GZMB | PD-1 | |

Figure 2:
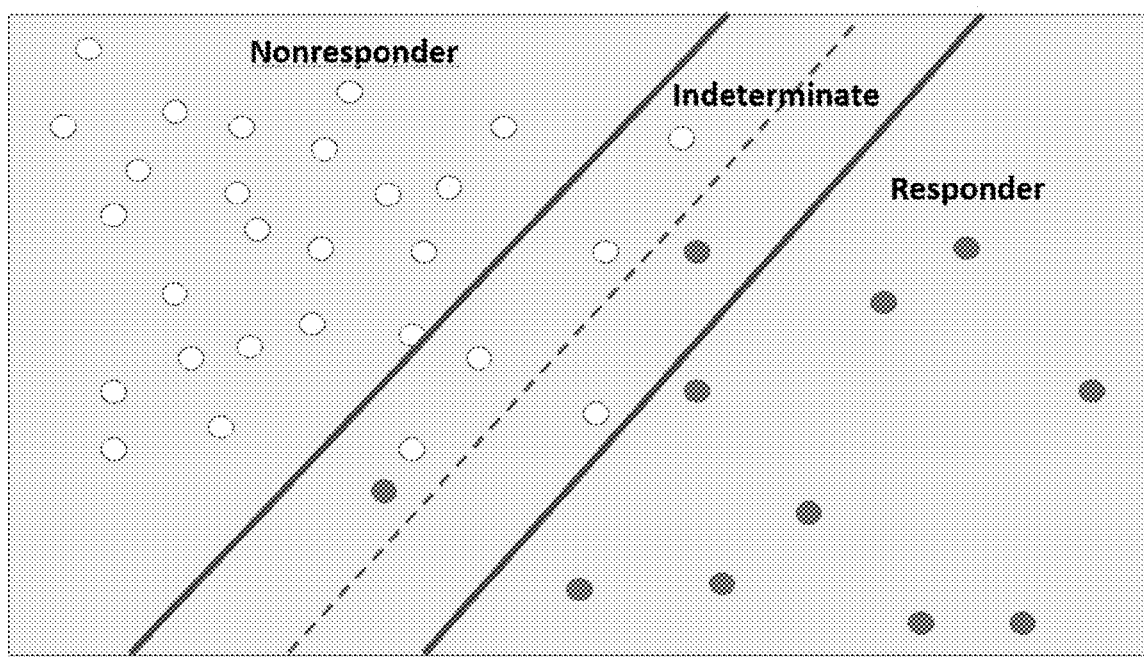
FIG. 2 is a schematic representation of feature space for a model utilizing the 54 genes and the mutation burden (MuB), in accordance with an embodiment.

Referring to FIG. 2, in one embodiment, is a schematic representation of feature space for a model utilizing the 54 genes, or 54 features, combined with mutational burden (MuB) as an additional feature. According to an embodiment, MuB, as an individual feature, is treated equally to the 54 genes, or 54 features.

In addition to listing genes that may be suitable for the 54 gene model, Table 2 also provides genes for which expression information can be utilized in the immune function model described herein. Accordingly, the genes listed in Table 2 may be utilized in one or more of the RNA-Seq, DNA-Seq, and mutation burden analyses.

TABLE 2

Genes Utilized for an Embodiment of the 54 Gene Model

| | | | | |
|---|---|---|---|---|
| ABCF1 | CIITA | HLA-B | MADCAM1 | PTPRC |
| ABL1 | CKS1B | HLA-C | MAF | PTPRCAP |
| ABL2 | CLEC4C | HLA-DMA | MAFB | PTPRD |
| ACVR2A | CMKLR1 | HLA-DMB | MAGEA1 | PTPRT |
| ADAMTS20 | CMPK1 | HLA-DOA | MAGEA10 | PVR |
| ADGRE5 | COL1A1 | HLA-DOB | MAGEA12 | PYGL |
| ADORA2A | CORO1A | HLA-DPA1 | MAGEA3 | RAD50 |
| AFF1 | CRBN | HLA-DPB1 | MAGEA4 | RAF1 |
| AFF3 | CREB1 | HLA-DQA1 | MAGEC2 | RALGDS |
| AIF1 | CREBBP | HLA-DQA2 | MAGI1 | RARA |
| AKAP9 | CRKL | HLA-DQB2 | MALT1 | RB1 |
| AKT1 | CRTAM | HLA-DRA | MAML2 | RECQL4 |
| AKT2 | CRTC1 | HLA-DRB1 | MAP2K1 | REL |
| AKT3 | CSF1R | HLA-E | MAP2K2 | RET |
| ALK | CSF2RB | HLA-F | MAP2K4 | RHOH |
| ALOX15B | CSMD3 | HLA-F-AS1 | MAP3K7 | RNASEL |
| APC | CTAG1B | HLA-G | MAPK1 | RNF2 |
| AR | CTAG2 | HLF | MAPK14 | RNF213 |
| ARG1 | CTLA4 | HMBS | MAPK8 | RORC |
| ARID1A | CTNNA1 | HNF1A | MARK1 | ROS1 |
| ARID2 | CTNNB1 | HOOK3 | MARK4 | RPS6 |
| ARNT | CTSS | HRAS | MBD1 | RPS6KA2 |
| ASXL1 | CX3CL1 | HSP90AA1 | MCL1 | RRM1 |
| ATF1 | CX3CR1 | HSP90AB1 | MDM2 | RUNX1 |
| ATM | CXCL1 | ICAM1 | MDM4 | RUNX1T1 |
| ATR | CXCL10 | ICK | MELK | S100A8 |
| ATRX | CXCL11 | ICOS | MEN1 | S100A9 |
| AURKA | CXCL13 | ICOSLG | MET | SAMD9 |
| AURKB | CXCL8 | ID2 | MIF | SAMHD1 |
| AURKC | CXCL9 | ID3 | MITF | SBDS |
| AXL | CXCR2 | IDH1 | MKI67 | SDHA |
| B3GAT1 | CXCR3 | IDH2 | MLANA | SDHB |
| BAGE | CXCR4 | IDO1 | MLH1 | SDHC |
| BAI3 | CXCR5 | IDO2 | MLL | SDHD |
| BAP1 | CXCR6 | IFI27 | MLL2 | SELL |
| BATF | CYBB | IFI35 | MLL3 | 9-Sep |
| BCL10 | CYLD | IFI44L | MLLT10 | SETD2 |
| BCL11A | CYP2C19 | IFI6 | MMP2 | SF3B1 |
| BCL11B | CYP2D6 | IFIH1 | MMP9 | SGK1 |
| BCL2 | DAXX | IFIT1 | MN1 | SH2D1A |
| BCL2L1 | DCC | IFIT2 | MPL | SH2D1B |
| BCL2L11 | DDB2 | IFIT3 | MPO | SIT1 |
| BCL2L2 | DDIT3 | IFITM1 | MRC1 | SKAP2 |
| BCL3 | DDR2 | IFITM2 | MRE11A | SLAMF7 |
| BCL6 | DDX58 | IFNA17 | MS4A1 | SLAMF8 |
| BCL9 | DEK | IFNB1 | MSH2 | SMAD2 |
| BCR | DGAT2 | IFNG | MSH6 | SMAD4 |
| BIRC2 | DICER1 | IGF1R | MTOR | SMARCA4 |
| BIRC3 | DMBT1 | IGF2 | MTR | SMARCB1 |
| BIRC5 | DNMT3A | IGF2R | MTRR | SMO |
| BLM | DPYD | IGSF6 | MUC1 | SMUG1 |
| BLNK | DST | IKBKB | MUTYH | SNAI1 |
| BMPR1A | EBI3 | IKBKE | MX1 | SNAI2 |
| BRAF | EFNA4 | IKZF1 | MYB | SOCS1 |
| BRCA1 | EGFR | IKZF2 | MYC | SOX11 |
| BRCA2 | EGR2 | IKZF3 | MYCL1 | SOX2 |
| BRD3 | EGR3 | IKZF4 | MYCN | SRC |
| BST2 | EIF2AK2 | IL10 | MYD88 | SRGN |
| BTK | EML4 | IL10RA | MYH11 | SSX1 |
| BTLA | ENTPD1 | IL12A | MYH9 | SSX2 |
| BUB1 | EOMES | IL12B | NBN | STAT1 |
| BUB1B | EP300 | IL13 | NCAM1 | STAT3 |
| C10orf54 | EP400 | IL15 | NCF1 | STAT4 |
| C1QA | EPHA3 | IL17A | NCOA1 | STAT5A |
| C1QB | EPHA7 | IL17F | NCOA2 | STAT6 |
| CA4 | EPHB1 | IL18 | NCOA4 | STK11 |
| CARD11 | EPHB4 | IL1A | NCR1 | STK36 |
| CASC5 | EPHB6 | IL1B | NCR3 | SUFU |
| CBL | ERBB2 | IL2 | NECTIN2 | SYK |
| CBLB | ERBB3 | IL21 | NF1 | SYNE1 |
| CCL17 | ERBB4 | IL21R | NF2 | TAF1 |
| CCL18 | ERCC1 | IL22 | NFATC1 | TAF1L |
| CCL2 | ERCC2 | IL23A | NFE2L2 | TAGAP |
| CCL20 | ERCC3 | IL2RA | NFKB1 | TAL1 |
| CCL21 | ERCC4 | IL2RB | NFKB2 | TAP1 |
| CCL22 | ERCC5 | IL2RG | NFKBIA | TARP |
| CCL3 | ERG | IL3RA | NIN | TBP |
| CCL4 | ESR1 | IL4 | NKG7 | TBX21 |
| CCL5 | ETS1 | IL6 | NKX2-1 | TBX22 |
| CCNB2 | ETV1 | IL6ST | NLRP1 | TCF12 |
| CCND1 | ETV4 | IL7 | NOS2 | TCF3 |
| CCND2 | EXT1 | IL7R | NOTCH1 | TCF7 |
| CCNE1 | EXT2 | ING4 | NOTCH2 | TCF7L1 |
| CCR1 | EZH2 | IRF1 | NOTCH3 | TCF7L2 |
| CCR2 | FAM123B | IRF4 | NOTCH4 | TCL1A |
| CCR4 | FANCA | IRF9 | NPM1 | TDO2 |
| CCR5 | FANCC | IRS1 | NRAS | TET1 |
| CCR6 | FANCD2 | IRS2 | NRP1 | TET2 |
| CCR7 | FANCF | ISG15 | NSD1 | TFE3 |
| CD14 | FANCG | ISG20 | NT5E | TFRC |
| CD160 | FANCJ | ITGA1 | NTN3 | TGFB1 |
| CD163 | FAS | ITGA10 | NTRK1 | TGFBR2 |
| CD19 | FASLG | ITGA9 | NTRK3 | TGM7 |
| CD1C | FBXW7 | ITGAE | NUMA1 | THBS1 |
| CD1D | FCER1G | ITGAL | NUP214 | TIGIT |
| CD2 | FCGR1A | ITGAM | NUP98 | TIMP3 |
| CD209 | FCGR2B | ITGAX | OAS1 | TLR3 |
| CD22 | FCGR3A | ITGB1 | OAS2 | TLR4 |
| CD226 | FCGR3B | ITGB2 | OAS3 | TLR7 |
| CD244 | FCRLA | ITGB3 | PAK3 | TLR8 |
| CD247 | FGFR1 | ITGB7 | PALB2 | TLR9 |
| CD27 | FGFR2 | ITK | PARP1 | TLX1 |
| CD274 | FGFR3 | JAK1 | PAX3 | TNF |
| CD276 | FGFR4 | JAK2 | PAX5 | TNFAIP3 |
| CD28 | FH | JAK3 | PAX7 | TNFAIP8 |
| CD33 | FLCN | JAML | PAX8 | TNFRSF14 |
| CD37 | FLI1 | JCHAIN | PBRM1 | TNFRSF17 |
| CD38 | FLT1 | JUN | PBX1 | TNFRSF18 |
| CD3D | FLT3 | KAT6A | PDCD1 | TNFRSF4 |
| CD3E | FLT4 | KAT6B | PDCD1LG2 | TNFRSF9 |
| CD3G | FN1 | KDM5C | PDE4DIP | TNFSF10 |
| CD4 | FOXL2 | KDM6A | PDGFB | TNFSF13B |
| CD40 | FOXM1 | KDR | PDGFRA | TNFSF14 |
| CD40LG | FOXO1 | KEAP1 | PDGFRB | TNFSF18 |
| CD44 | FOXO3 | KIAA0101 | PECAM1 | TNFSF4 |
| CD47 | FOXP1 | KIR2DL1 | PER1 | TNFSF9 |
| CD48 | FOXP3 | KIR2DL2 | PGAP3 | TNK2 |
| CD52 | FOXP4 | KIR2DL3 | PGF | TOP1 |
| CD53 | FUT4 | KIT | PHOX2B | TOP2A |
| CD6 | FYB | KLF2 | PIK3C2B | TP53 |
| CD63 | FZR1 | KLF6 | PIK3CA | TP63 |
| CD68 | G6PD | KLRB1 | PIK3CB | TPR |
| CD69 | GADD45GIP1 | KLRD1 | PIK3CD | TRIM24 |
| CD70 | GAGE1, GAGE12I, GAGE12F | KLRF1 | PIK3CG | TRIM29 |
| CD74 | GAGE10 | KLRG1 | PIK3R1 | TRIM33 |
| CD79A | GAGE12J | KLRK1 | PIK3R2 | TRIP11 |
| CD79B | GAGE13 | KRAS | PIM1 | TRRAP |
| CD80 | GAGE2C, GAGE2A, GAGE2E | KREMEN1 | PKHD1 | TSC1 |
| CD83 | GATA1 | KRT5 | PLAG1 | TSC2 |
| CD86 | GATA2 | KRT7 | PLCG1 | TSHR |
| CD8A | GATA3 | LAG3 | PLEKHG5 | TUBB |
| CD8B | GBP1 | LAMP1 | PMEL | TWIST1 |
| CDC73 | GDNF | LAMP3 | PML | TYROBP |
| CDH1 | GNA11 | LAPTM5 | PMS1 | UBR5 |
| CDH11 | GNAQ | LCK | PMS2 | UGT1A1 |
| CDH2 | GNAS | LCN2 | POLR2A | USP9X |
| CDH20 | GNLY | LEXM | POT1 | VCAM1 |
| CDH5 | GPR124 | LIFR | POU2AF1 | VEGFA |
| CDK1 | GPR18 | LILRB1 | POU5F1 | VHL |
| CDK12 | GRAP2 | LILRB2 | PPARG | VTCN1 |
| CDK4 | GRM8 | LMNA | PPP2R1A | WAS |
| CDK6 | GUCY1A2 | LPHN3 | PRDM1 | WHSC1 |
| CDK8 | GUSB | LPP | PRF1 | WRN |
| CDKN2A | GZMA | LRG1 | PRKAR1A | WT1 |
| CDKN2B | GZMB | LRP1 | PRKDC | XAGE1B |
| CDKN2C | GZMH | LRP1B | PSIP1 | XPA |
| CDKN3 | GZMK | LST1 | PSMB9 | XPC |
| CEACAM1 | HAVCR2 | LTF | PTCH1 | XPO1 |
| CEACAM8 | HCAR1 | LTK | PTEN | XRCC2 |
| CEBPA | HERC6 | LY9 | PTGS2 | ZAP70 |

TABLE 2-continued

Genes Utilized for an Embodiment of the 54 Gene Model

| CHEK1 | HGF   | LYZ    | PTK7   | ZBTB46 |
|-------|-------|--------|--------|--------|
| CHEK2 | HIF1A | M6PR   | PTPN11 | ZEB1   |
| CIC   | HLA-A | MAD2L1 | PTPN6  | ZNF384 |
|       |       |        | PTPN7  | ZNF521 |

Model #2—The 4 Gene Model

According to an embodiment, the 4 gene model utilizes a decision tree model to select the best minimal set of TILs or T-cell activation genes for prediction. The 4-gene model was derived, for example, with an independent decision tree machine learning approach from the initial selection of 54 genes, although other genes are possible. The machine learning algorithm selected a subset of genes and built a human-interpretable decision tree that best distinguishes the responders and nonresponders from the whole population of 87 training samples. The automatically selected four genes includes two genes related to T-cell activation, a gene related to immune response regulation and a gene related to cytokine signaling.

Figure 3:
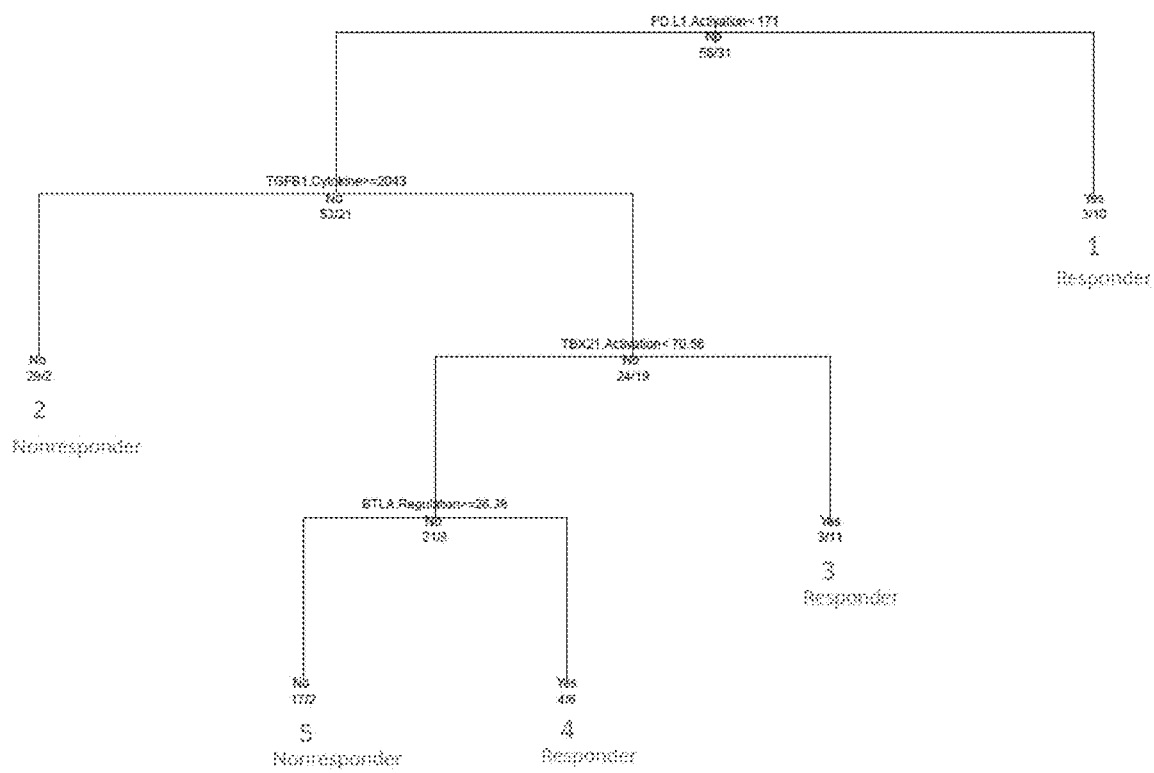
FIG. 3 is a schematic representation of a decision tree for a 4 gene model, in accordance with an embodiment.

Referring to FIG. 3, in one embodiment, is a schematic representation of a decision tree for the 4 gene model. The identity of the four genes utilized, and the specific cut-off values, in the 4 gene model can vary. According to one embodiment, the four genes are PD-L1, TGFB1, TBX21, and BTLA, and the cut-off values for each of these genes are 171, 2043, 70.56, and 26.38, respectively. According to a further embodiment, the first gene is PD-L1, the second gene is TGFB1, the third gene is TBX21, and the fourth gene is BTLA. The decision tree provides a series of YES or NO decisions utilizing the expression level (in normalized reads per million (nRPM)) of each gene. For example, if the nRPM of gene 1 is less than a certain threshold or cutoff, the tumor is determined to be a responder. If the nRPM of gene 1 is more than the threshold or cutoff, the decision tree proceeds to the next gene. The results of the decision tree classify the tumor as either a responder or a non-responder, as shown in FIG. 3.

According to one embodiment, not shown in FIG. 3, the 4 gene model can be determined or designed to classify tumors as being a responder or non-responder to a therapy, and can also be determined or designed to predict the risk of hyper-progression of cancer. For example, the 4 gene model can be determined or designed to identify a subset of non-responders that have a risk of hyper-progressive disease. The risk of hyper-progressive disease may be qualitative and/or quantitative.

Figure 4:
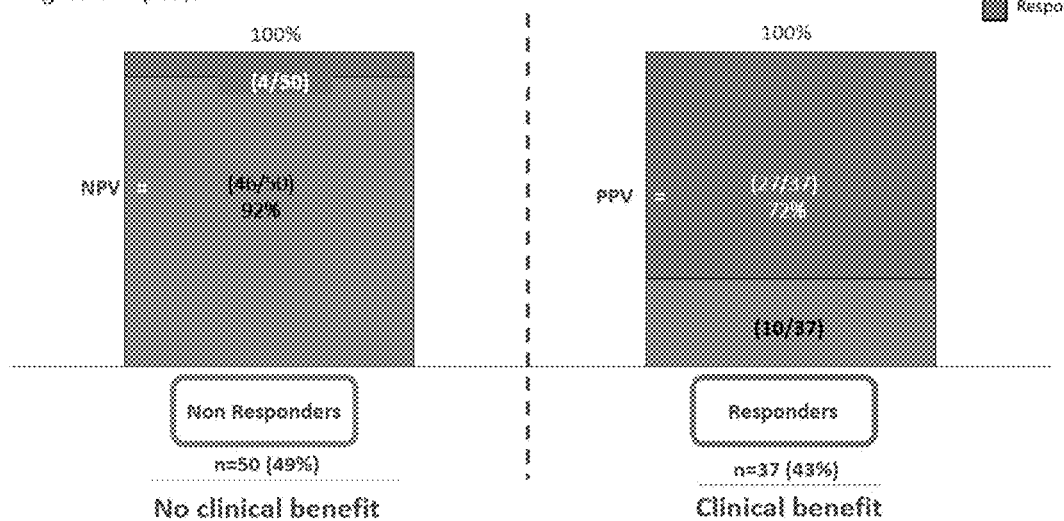
FIG. 4 is a graph of results for the 4 gene model using a panel of retrospective samples for training, in accordance with an embodiment.

Referring to FIG. 4, in one embodiment, is a graph of results for the 4 gene model using a panel of 87 retrospective samples for training. As shown in the graph, the results have a PPV of 72% for 43% of the population, a NPV of 92% for 49% of the population, and no indeterminate group.

Model #3—The Immune Function Model

According to an embodiment, the immune function model utilizes 13 genes representing immune cell infiltration, 23 genes for T-cell activation, 10 genes for cytokine signaling, and 8 genes for immune response regulation, although other genes are possible. The immune function model utilizes a decision tree learning method, similar to the 4-gene model. However, instead of evaluating each individual gene's predictive importance, the immune function model takes the weighted average relative rank of multiple genes in a given immune functional group that include immune cell infiltration, immune response regulation, T-cell activation, and cytokine signaling. The relative rank is established by ranking a gene's normalized expression value (nRPM) against those of a reference population, and further normalizing the rank into a same range from 0 to 100. The immune function relative rank collectively reflects the degree of expressions of multiple genes with same function in comparison to a reference population.

Figure 5:
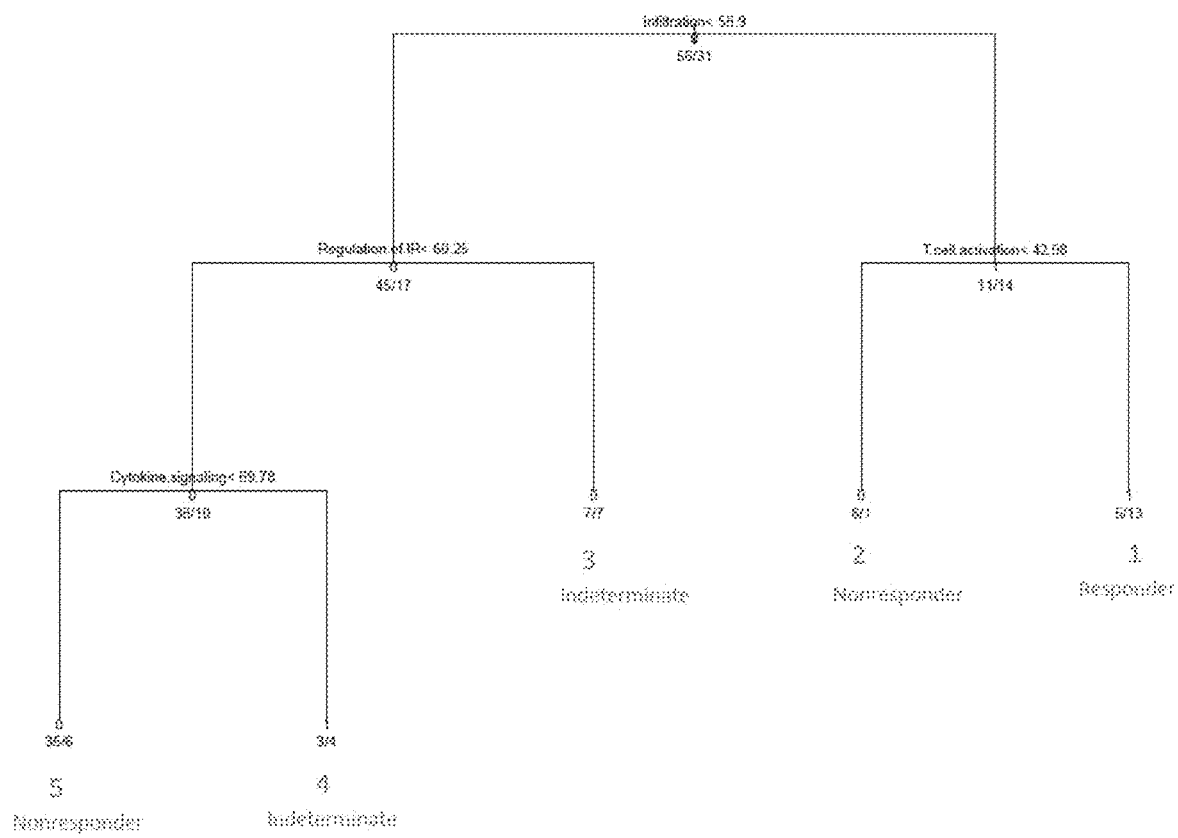
FIG. 5 is a schematic representation of a decision tree for an immune function model, in accordance with an embodiment.

Referring to FIG. 5, in one embodiment, is a schematic representation of a decision tree for the immune function model. The identity of the gene sets can vary. The decision tree provides a series of YES or NO decisions utilizing a relative rank cutoff for each of the four different immune functional groups (immune cell infiltration, immune response regulation, T-cell activation, and cytokine signaling), and can classify tumors as being a responder to therapy, a non-responder to therapy, or an indeterminate responder to therapy.

According to one embodiment, not shown in FIG. 5, the immune function model can be determined or designed to classify tumors as being a responder, indeterminate responder, or non-responder to a therapy, and can also be determined or designed to predict the risk of hyper-progression of cancer. According to one embodiment, the four functions are immune cell infiltration, immune response regulation, T-cell activation, and cytokine signaling, and the cut-off values for each of these functions are 58.9, 60.25, 42.98 and 69.78, respectively. For example, the immune function model can be determined or designed to identify a subset of non-responders that have a risk of hyper-progressive disease. The risk of hyper-progressive disease may be qualitative and/or quantitative.

Figure 6:
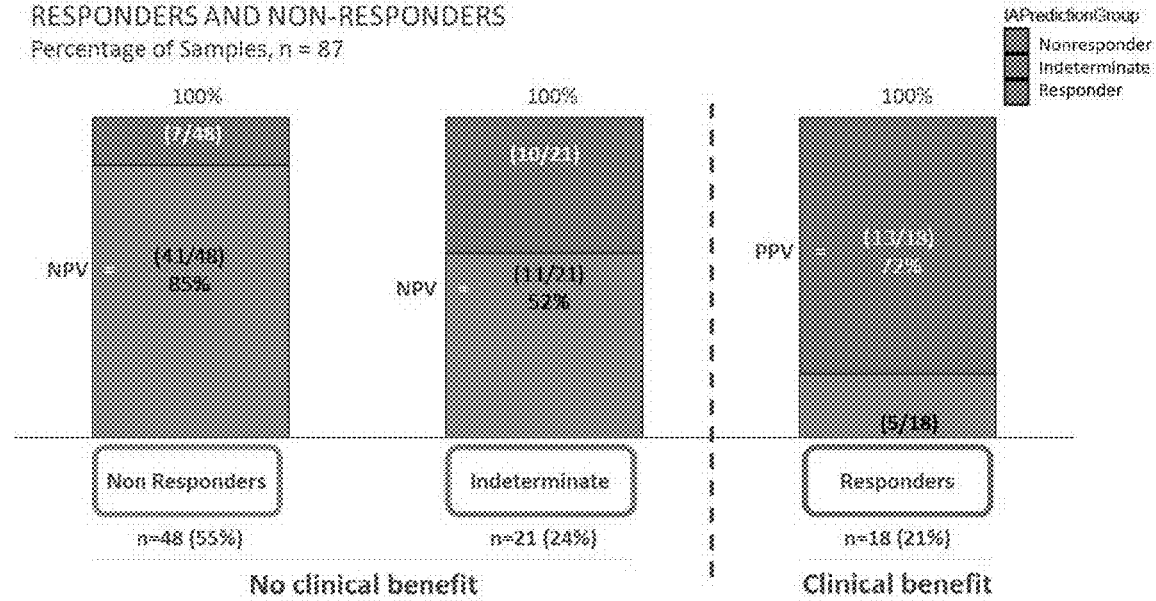
FIG. 6 is graph of results for an immune function model using a panel of retrospective samples for training, in accordance with an embodiment.

Referring to FIG. 6, in one embodiment, is a graph of results for the immune function model using a panel of 87 retrospective samples for training. As shown in the graph, the results have a PPV of 72% for 21% of the population, a NPV of 85% for 55% of the population, and an indeterminate group representing 24% of the population.

According to an embodiment, the immune function model utilizes expression information for 54 genes (13 genes representing immune cell infiltration, 23 genes for T-cell activation, 10 genes for cytokine signaling, and 8 genes for immune response regulation), although many other gene combinations are possible, including but not limited to the genes identified in Table 2. Table 3 includes a list of genes for which expression information can be utilized in the immune function model.

TABLE 3

Genes Utilized for an Embodiment of the Immune Function Model

| Immune cell infiltration genes (13) | T-cell activation genes (23) | Cytokine signaling genes (10) | Immune response regulation genes (8) |
|---|---|---|---|
| CD8A | CD27 | CD274 (PD-L1) | IL10 | ADORA2A |
| CD8B | CD28 | PDCD1LG2 (PD-L2) | IL1B | GATA3 |
| CD3D | CD40 | CTLA4 | TNF | CD38 |
| CD3E | CD40LG | OX40 | TGFB1 | ENTPD1 (CD39) |
| CD3G | CD80 | OX40LG | CCR2 | IDO1 |
| CD2 | CD86 | GZMB | MX1 | KLRD1 |
| CD4 | TNFRSF9 (CD137) | IFNG | CXCR6 | STAT1 |
| FOXP3 | TNFRSF18 (GITR) | TNFRSF14 | CXCL10 | BTLA |

TABLE 3-continued

Genes Utilized for an Embodiment of the Immune Function Model

| Immune cell infiltration genes (13) | T-cell activation genes (23) | | Cytokine signaling genes (10) | Immune response regulation genes (8) |
|---|---|---|---|---|
| CD68 | ICOS | TBX21 | | DDX58 |
| CD163 | ICOSLG | VISTA | | CCL2 |
| MS4A1 (CD20) | LAG3 | | | |
| CSF1R | HAVCR2 (TIM3) | | | |
| SLAMF4 | PDCD1 (PD-1) | | | |

Model #4—The Primary Immune Marker Model

The primary immune marker model or approach is optional, and analyzes one or more immune markers utilizing immunohistochemistry. According to an embodiment, the primary immune marker model or approach analyzes PD-L1 protein expression and/or tumor infiltrating lymphocyte (TIL) expression (including but not limited to CD3 and/or CD8) using immunohistochemistry. According to another embodiment, the primary immune marker model or approach analyzes PD-L1 and/or PD-L2 copy number gain utilizing fluorescent in situ hybridization (FISH) methodology.

Multiple Model Correlation

According to an embodiment, the output from two or more of the 54 gene model, the 4 gene model, and the immune function model are combined to provide a final recommendation for personalized oncology therapies.

Figure 7:
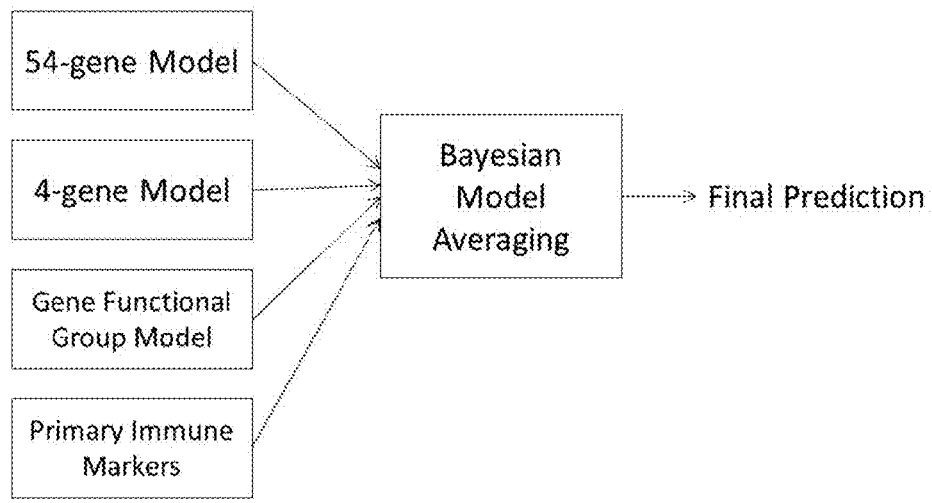
FIG. 7 is a schematic representation of a Bayesian Model Averaging (BMA) for final prediction using output from the 54 gene model, the 4 gene model, and the immune function model, in accordance with an embodiment.

For example, referring to FIG. 7, in one embodiment, output from the 54 gene model, the 4 gene model, and the immune function model were combined using a Bayesian Model Averaging (BMA) for final prediction. According to an embodiment, the BMA algorithm is similar to the concept of majority voting, however, the algorithm also takes advantage of each individual model's performance prior probability distribution to optimize the final prediction.

According to a further embodiment as shown in FIG. 7, output from the 54 gene model, the 4 gene model, the immune function model, and the primary immune marker model were combined using a BMA for a final prediction.

Figure 8:
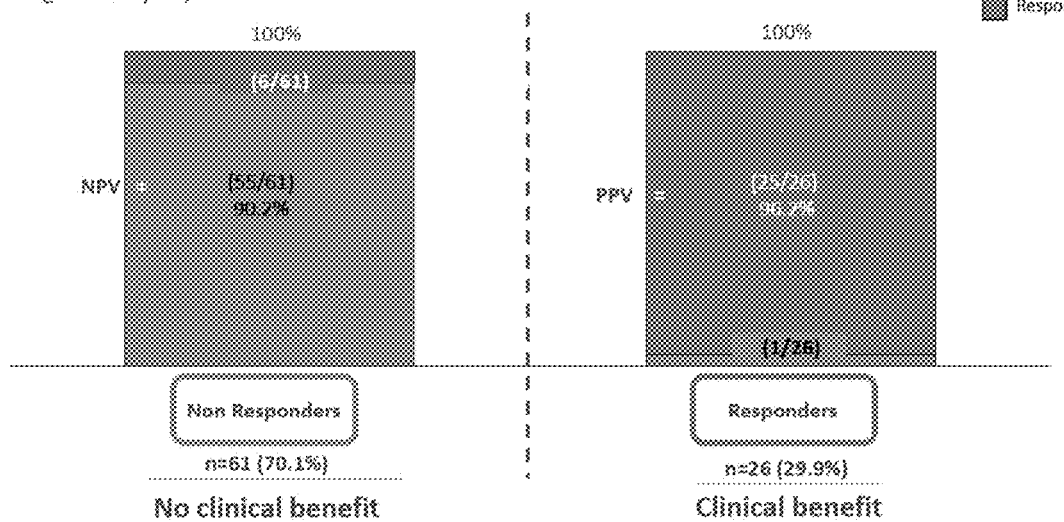
FIG. 8 is a graph of results for Bayesian Model Averaging using a panel of 87 retrospective samples for training, and results from the 54 gene model, the 4 gene model, and the immune function model, in accordance with an embodiment.

Referring to FIG. 8, in one embodiment, is a graph of results for the BMA using a panel of 87 retrospective samples for training, and results from the 54 gene model, the 4 gene model, and the immune function model. As shown in the graph, the results have a PPV of 96% for 30% of the population, a NPV of 90% for 70% of the population, and no indeterminate group.

Referring to FIG. 9, in one embodiment, is a table of overall results from each of the 54 gene model, the 4 gene model, the immune function model, and the Bayesian Model Averaging (BMA).

The various approaches and models described or otherwise envisioned herein utilize a retrospective training panel and machine learning to derive a 54 gene model, a 4 gene model, and an immune function model. As the various approaches and models utilize larger and/or different retrospective training panels, the various genes and models may vary.

The Immune Report Card

Figure 10:
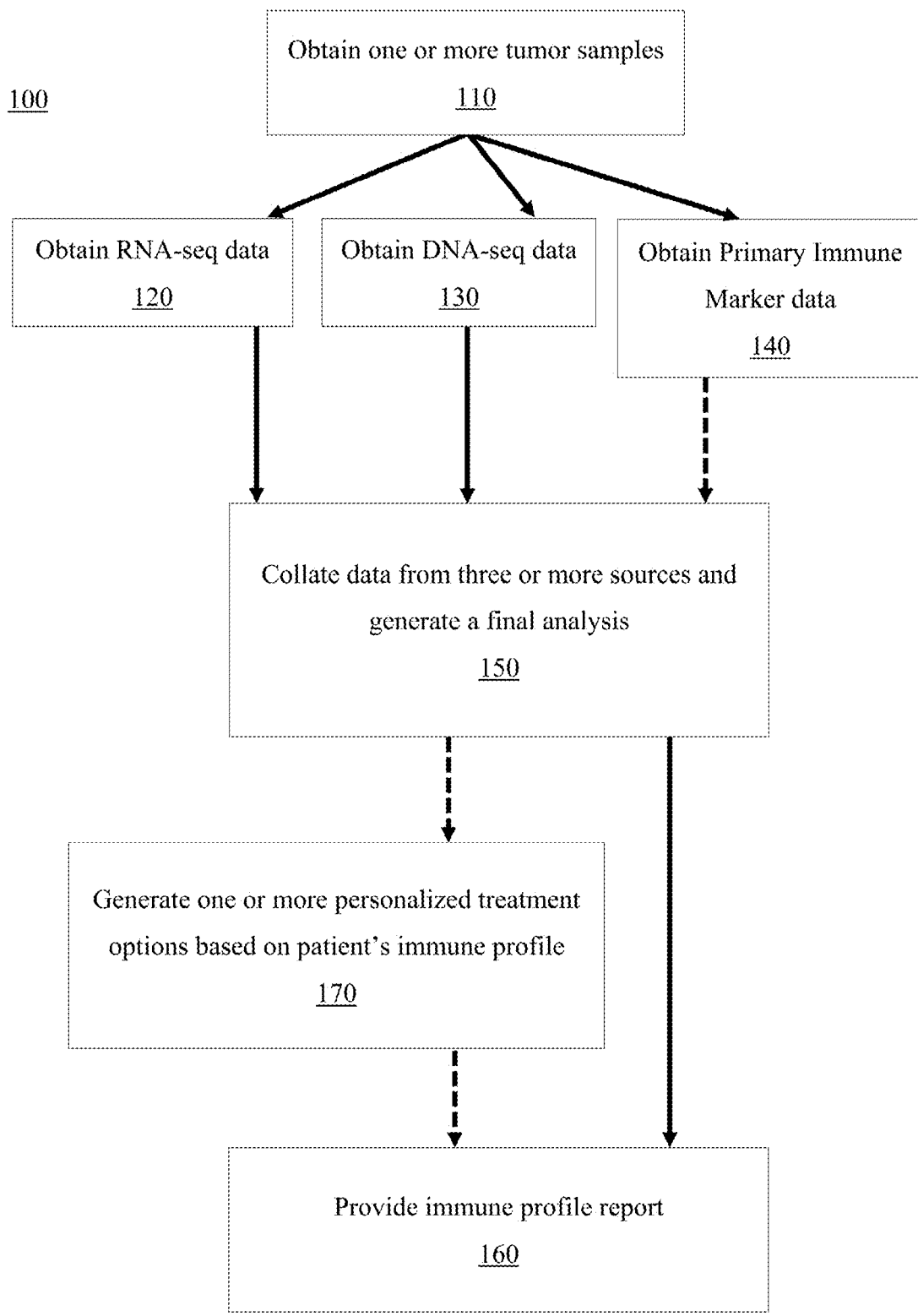
FIG. 10 is a flowchart of a method for providing a report to a patient's clinician, in accordance with an embodiment.

Referring to FIG. 10 is a method 100 for generating a report comprising a likelihood of a patient's tumor microenvironment to respond to immunotherapy. According to an embodiment, the report also comprises one or more personalized treatment options based on the patient's comprehensive immune profile. According to an embodiment, the method utilizes three or more of five data inputs to generate the data necessary to determine the likelihood(s) and the personalized treatment options. According to an embodiment, those five data inputs can comprise at least:

1. RNA-seq to measure relative transcript levels of genes associated with tumor infiltrating lymphocytes (TILs) and T-cell receptor signaling (TCRS) genes associated with anti-cancer immune response and immunotherapeutic targets;
2. DNA-seq to estimate mutational burden (MUB);
3. Immunohistochemistry (IHC) to measure PD-L1 protein expression and pattern of tumor infiltrating lymphocytes (TILS) expression (CD3 and CD8);
4. PCR to assess microsatellite instability (MSI); and/or
5. Fluorescent in situ hybridization (FISH) to detect PD-L1/L2 copy number gain Accordingly, at step 110 of the method, one or more tumor samples or specimens are collected. The samples may be collected using any method now known or developed in the future. The sample may be obtained directly from the patient and/or tumor, or may be obtained from a sample previously obtained from the patient and/or tumor. The sample may be a tumor sample, or may be a non-tumor sample obtained from an individual. The sample may be analyzed immediately, and/or may be stored for future analysis. Accordingly, the sample may be processed for shipping, storage, and/or for any other current or future use.

At step 120 of the method, RNA-seq data input is obtained. According to an embodiment, the RNA-Seq data input comprises a next generation sequencing (NGS) assay that uses amplicon-based targeted NGS for digital gene expression detection to interrogate 395 genes representing immune-related gene functions. One embodiment may be focused on 54 of these 395 genes, with an additional 10 genes used as controls. In this or other embodiments, one or more additional genes—such as the genes listed in one or more of the tables herein—may be analyzed and provided in the method results.

According to an embodiment, the TILs gene component of the RNA-seq data input comprises genes identified to classify subsets of infiltrating immune cells. The genes may be the 11 genes identified herein (CD163, CD2, CD3D, CD3E, CD3G, CD4, CD68, CD8A, CD8B, FOXP3, and CD20), or may comprise different and/or additional genes. The application of TILs as predictive immune biomarkers or prognostic markers of survival has been studied in a wide variety of tumor types. Evidence has shown that CD3+ CD8+ cytotoxic lymphocytes are positively associated with response to CPIs, while FOXP3+ Tregs have a negative association. The pattern of TILs in a tumor has also been shown to have importance.

According to an embodiment, the T-cell receptor signaling (TCRS) component of the RNA-seq data input comprises genes expressed on immune infiltrating cells, neoplastic cells, or other cells of the tumor microenvironment, and are classified by Immune Phenotypes as either directly involved in checkpoint blockade or other functions related to the adaptive immune response. The genes may be the 43 genes identified herein (see, e.g., Table 1), or may comprise different and/or additional genes.

According to an embodiment, Immune Phenotypes associated with checkpoint blockade are typically classified as a receptor and associated ligand. According to the subset of TCRS associated genes, either the ligand or the receptor is expressed by one or more subsets of T-cells. Genes related to checkpoint blockade can be further divided into those that are the direct target of one or more checkpoint inhibitor drugs versus those that are not. Direct targets of checkpoint inhibitor drugs may be either the receptor or ligand, but not both simultaneously. An example of a checkpoint inhibitor drug and target is ipilimumab and the receptor CTLA-4 that is expressed on activated T-cells. According to an embodiment, the report of likelihood(s) and the personalized treatment options also reports genes related to checkpoint blockade, as Checkpoint Blockade (PD-1, CTLA-4), Checkpoint Blockade (Other), or T-cell Primed, as shown in Table 3. Checkpoint Blockade and Checkpoint Blockade (Other) are related to co-inhibitory signaling for effector T-cells, while T-cell Primed is co-stimulatory. Other immune phenotypes that are associated with the adaptive immune response that indirectly impact TCRS include Myeloid Suppression, Pro-inflammatory Response, Anti-inflammatory Response, and Metabolic Immune Escape.

TABLE 3

Analyzed immune phenotypes.

| Immune Phenotype | Key Markers | Action |
|---|---|---|
| Checkpoint Blockade (PD-1/CTLA4) | PD-L1, PD-1, CTLA4, PD-L2 | T-cell Inhibition |
| Checkpoint Blockade (Other) | BTLA, LAB3, VISTA (B7-H5), TIM3, TNFRSF14 (HVEM; CD270) | T-cell Inhibition |
| T-cell Primed | CD27, CD28, CD40, CD40LG, TNFRSF9 (CD137), TNFRSF18 (GITR), ICOS, ICOSLG, OX40, OX40LG, INFG, GZMB, TBX21 (T-bet) | T-cell Activation |
| Myeloid Suppression | CSF1R, CD68, CD163, CCR2, CCL2 | Promote M2 TAMs |
| Anti-Inflammatory Response | IL10, TGFB1 | Promote MDSCs |
| Metabolic Immune Escape | IDO1, ADORA2A, CD39 | Self-amplifying T-reg loop |
| Pro-Inflammatory Response | CXCL10, CXCR6, IL1B, STAT1, TNF, DDX58, MX1 | Promote NK T-cell functions |

The expression of each gene is compared to a reference population, normalized to a value between 1 and 100, and referred to as the relative rank. According to one embodiment, the baseline reference population for this method consisted of RNA-seq results derived from 167 unique tumors. The top 95th percentile of scores, or relative rank, which are values equal to or greater than 95 are interpreted as very high expression, while the 85th to 94th percentile are interpreted as high expression. The bottom 50th percentile of scores, or relative rank, which are values less than 49 are considered low or very low expression. Scores between 50 and 85 are considered moderate expression. The interpretation of immune phenotypes is derived from the mean of all genes for that class and are ranked as normalized values in the same manner as expression of individual genes.

At step 130 of the method, of the method, DNA-seq data input is obtained. According to an embodiment, the DNA-Seq data input comprises a 1.75 Mb AmpliSeq capture of 409 oncogenes with full exon coverage that evaluates a total of 6,602 exons covering 1,165,294 base pairs of unique exon DNA in an all-exon mutational profiling assay. Mutational Burden (MUB) is reported as the number of mutations per megabase (Mb) of exonic DNA. MuB can be calibrated against a subset of samples with whole exome sequencing for development of a variant calling pipeline that provides 20× coverage at >=90% of the unique exon DNA in the IRC panel. According to an embodiment, the MuB was calibrated against four clinically relevant peer-reviewed publications reporting a correlation of high mutational burden with response to checkpoint inhibitors in melanoma. Using an equivalent whole exome and these four references as a calibrator the cut-off values for MuB as measured by number of mutations per Mb DNA was established using an internal reference population of 167 patients. In this regard MuB is classified as "very high", "high", "intermediate", "low", and "very low". While classifications of high and very high MuB are more likely to be responders, as a single biomarker, this measurement lacks sensitivity and specificity, and should not be used independently of other assay results in IRC.

At step 140 of the method, immunohistochemistry data input is obtained. According to an embodiment, the immunohistochemistry data input comprises a measurement of PD-L1 protein expression and tumor infiltrating lymphocytes (TILS) expression (CD3 and CD8). According to an embodiment, the immunohistochemistry data input is obtained utilizing an automated DAKO platform and commercially available antibodies to provide expression data for PD-L1, CD3 and CD8. The method can report protein expression patterns for all three analytes to better define the multi-dimensional interactions that occur in the tumor microenvironment, as well as a semi-quantitative measurement of expression for PD-L1.

According to an embodiment, for melanoma, PD-L1 is performed using the PD-L1 IHC 28-8 FDA approved assay, and follows scoring guidelines for reporting the percentage of neoplastic cells displaying membranous staining of any intensity. The PD-L1 22C3 FDA approved assay is used to test non-small cell lung cancer and other tumor types, with PD-L1 protein expression determined by using Tumor Proportion Score (TPS), which is the percentage of viable tumor cells showing partial or complete membrane staining at any intensity.

According to an embodiment, the TILS expression pattern (CD3 and CD8 as measured by IHC) is reported as "infiltrating", "non-infiltrating", or "minimal to absent". An "infiltrating" pattern refers to staining of TILs within groups of neoplastic cells in the majority of the tumor examined. "Non-infiltrating" refers to TILs present, but inconsistent pattern of infiltrating groups of neoplastic cells in the majority of the tumor examined. The non-infiltrating pattern of staining for CD3 and CD8 includes cases with an abundance of TILs at the advancing edge of the tumor, but without infiltration of the neoplastic cells. The minimal to absent pattern is essentially minimal to no TILs present within any part of the tumor.

According to an embodiment, CD3 highlights T-cells (referred to as TILs in this assay) and is useful to identify the T-cell population associated with the neoplasm. CD8 highlights cytotoxic T-cells which (when found in the midst of neoplastic cells) tend to be reflective of response to checkpoint inhibitors (CPIs). The information provided in this report may be used by physicians to decide if immunotherapy with one or more FDA-approved checkpoint inhibitors may benefit this patient.

According to one embodiment, the PCR component of the method uses five markers including two mononucleotide repeat markers (BAT-25, BAT-26) and three dinucleotide repeat markers (D2S123, D5S346 and D17S250) to detect microsatellite instability (MSI). According to another embodiment, the NGS component of the method uses up to 100 homopolymer, dinucleotide, trinucleotide and/or tetranucleotide markers to detect microsatellite instability (MSI).

In either case, the results are reported as "MSI-high", "MSI-low", or "MSS" (microsatellite stable). MSI typically used as a prognostic marker of survival in the setting of Lynch syndrome, also called hereditary nonpolyposis colorectal cancer (HNPCC), is an FDA marker of response to checkpoint inhibitors in colorectal cancer and second line treatment in solid tumors with no other therapeutic options.

Colorectal carcinoma, endometrial carcinomas, and other types of neoplasms with MSI-H may be sporadic (ie, microsatellite instability is found only in the neoplasm and is therefore not part of a hereditary condition) or secondary to Lynch syndrome, a hereditary condition (ie, related to a familial genetic mutation in a DNA repair gene, typically MLH1, PMS2, MSH2, or MSH6). Although an MSI test can determine the presence of microsatellite instability it cannot determine which specific DNA-repair gene is affected. Immunohistochemistry against MLH1, PMS2, MSH2, or MSH6 can be used to find the specific protein that is affected. Depending on the expression loss pattern and the carcinoma tissue of origin, slightly different strategies are indicated. For specifics, a review of the National Comprehensive Cancer Network (NCCN) guidelines is recommended. The presence of Lynch syndrome is definitely determined when a pathogenic DNA-repair gene mutation is found in non-neoplastic tissue from the patient. In such cases, genetic counseling is recommended with involvement of family members who are at risk of also having Lynch syndrome. MSI-H colorectal cancers (both sporadic and Lynch syndrome related) are known to have a different clinical profile (prognosis and chemotherapy responsiveness) from MSS (microsatellite stable) colorectal cancers.

According to an embodiment, the FISH component of the method measures copy number of PD-L1 (CD274) and PD-L2 (PDCD1LG2), two PD-1 ligands that when amplified are associated with PD-L1 expression. The two genes are located 40 kb apart on 9p24.1 and are detected using a pool of fluorescently labeled BAC clones that map to the gene region (RP11-635N21, RP11-812M23 and RP11-485M14). The results are reported using ASCO-CAP HER2 Test Guideline Recommendations for determining copy number as amplified, equivocal, or not amplified. An amplified result is when the ratio of PD-L1/2 to CEP9 is equal to or greater than 2.0 for any copy number value of PD-L1/2, or when the ratio of PD-L1/2 to CEP9 is less than 2.0 and the copy number value of PD-L1/2 is equal to or greater than 6.0. An equivocal result occurs when the ratio of PD-L1/2 to CEP9 is less than 2.0 and the copy number value of PD-L1/2 is equal to or greater than 4.0 and less than 6.0. A not amplified result occurs when the ratio of PD-L1/2 to CEP9 is less than 2.0 and the copy number value of PD-L1/2 is equal to or greater than 4.0. IRC uses the prior NYS-CLEP approved OmniSeq "PD-L1 and PD-L2 amplification and Validation Data SOP" for PD-L1/2 copy number testing.

At step 150 of the method, the data input from one or more of steps 120, 130, and 140 is collated and analyzed. For example, according to an embodiment, the output are combined to provide a final recommendation for personalized oncology therapies. For example, according to an embodiment, the output are combined using a Bayesian Model Averaging (BMA) for final prediction. According to an embodiment, the BMA algorithm is similar to the concept of majority voting, however, the algorithm also takes advantage of each individual model's performance prior probability distribution to optimize the final prediction. However, many other methods for collating the data from the two or more data inputs are possible.

At step 160 of the method, a clinical report is provided to the patient's clinician. The report comprises at least a likelihood of the patient's tumor microenvironment to respond to particular immunotherapies, and/or combination immunotherapies, and/or immunotherapy clinical trials. According to an embodiment, at step 170 of the method the data inputs, collated data, and/or final analysis is utilized to generate one or more personalized treatment options based on the patient's comprehensive immune profile. Thus, the report provided to the patient may also comprise one or more personalized treatment options.

According to an embodiment, the report provided to the patient's clinician can comprise one or more of the following:

Priority Immune Markers—At-a-glance information for clinically relevant immune markers for therapeutic management including but not limited PD-L1 expression, pattern and expression of tumor infiltrating lymphocytes (TILS), microsatellite instability (MSI) mutational burden (MUB), and PD-L1/L2 copy number gain. Evidence for therapeutic associations for each marker can be provided in the context of the tumor type tested.

Summary Interpretation—Pathologist interpretation and characterization of the overall immune status of this tumor based on both priority immune markers and TCRS gene expression. The Summary Interpretation can provide an assertion of likelihood of response to FDA approved checkpoint inhibitors and an overview of clinical trial opportunities trials based on immune phenotype assessment.

Immune Phenotypes Summary—Overview of gene expression for several immune phenotypes, showing highly expressed genes within each phenotype as applicable. The genes associated with each immune phenotype are not intended to be all inclusive of genes with a similar or identical action, but rather are genes for which expression was rigorously validated. Some genes within a given immune phenotype are associated immunotherapeutic agents available as either FDA-approved therapies or clinical trials.

Immune Phenotype Details—Gene level expression rank and interpretation of TCRS genes by immune phenotype. The expression of each gene is provided as a rank and interpretations as previously described in the RNA-Seq component. Immunotherapies associated with genes are listed without regard to tumor type tested. With the exception of PD-L1, evidence supporting over-expression of any immune phenotype gene and response to any associated immunotherapy, may be limited.

Tumor Infiltrating Lymphocytes—Gene level expression rank and interpretation of TILS genes associated with differentiation of various immune-related cells.

Clinical Trials—Clinical trials are displayed for the tumor type tested, for over-expressed markers with therapies in clinical development that are ranked high or very high. When there are no markers ranked high or very high, clinical trials are displayed for markers ranked moderately high. Trials related to the recruitment of lymphocytes into the tumor are always displayed when a tumor is considered non-inflamed.

Example—Analyzing Immune Response in Solid Tumors

According to an embodiment, the methodologies described or otherwise envisioned herein were utilized to analyze immune response in formalin-fixed paraffin-embedded (FFPE) tumor specimens, in order to provide a characterization of the immunological tumor microenvironment as a guide for therapeutic decisions on patients with solid tumors.

As described herein, the analysis utilized RNA-seq data to semi-quantitatively measure the levels of transcripts related to anticancer immune responses and transcripts reflecting the relative abundance of tumor-infiltrating lymphocytes (TILs), as well as on DNA-seq data to estimate mutational burden. Although not described in this example, the analysis could comprise primary marker immune data as described or otherwise envisioned herein.

An embodiment of a methodology for obtaining and/or analyzing RNA-seq data and DNA-seq data is described below. However, it is understood that this is just one possible embodiment, and is therefore not limiting in any way. Other methodologies for obtaining and/or analyzing RNA-seq data and DNA-seq data are possible.

This assay, unlike existing mutational profiling assays, accurately matches patients to immunotherapeutic treatments based on the immunological configuration of their tumor, using a wide range of biomarkers.

Methods

In order to evaluate the analytical performance of the assay, 167 FFPE specimens and a subset of matched fresh frozen (FF) tissues from NSCLC, melanoma, renal cell carcinoma, head and neck squamous cell carcinoma (HN-SCC), and bladder cancer patients were obtained. Specimens were collected under an institutional banking policy with informed patient consent, the study was approved by an internal review board review (IRB Protocol #BDR 073116) as per institutional policy for non-human subjects research.

The specimen included fine-needle aspiration biopsies, punch biopsies, needle core biopsies, incisional biopsies, excisional biopsies, and resection specimens from 2002-2016. For a subset of specimens, whole-exome sequencing and whole-transcriptome RNA-seq data were available as part of The Cancer Genome Atlas (TCGA) project for comparative purposes. Four human cell lines, lymphoblastoid GM12878 cells (ATCC, Manassas, Va.), colorectal cancer KM-12 cells (NCI-Frederick Cancer DCTD, Bethesda, Md.), NSCLC HCC-78 cells (DSMZ, Braunschweig, Germany), and large cell lymphoma SU-DHL-1 cells (ATCC) processed as FFPE blocks were also used for development and as internal run controls.

A board-certified anatomical pathologist reviewed a hematoxylin and eosin (H&E)-stained tumor section to identify the region(s) to be tested. Tumor surface area on the H&E-stained section was ≥2 mm2 per slide, with tumor cellularity ≥50% and necrosis ≤50%. For the examination of potential pre-analytic interferences, non-malignant and necrotic tissues were also macro-dissected from corresponding unstained slides for nucleic acid extraction. Regions identified by the pathologist were used as guides to scrape tissue from 3-5 unstained slides. Genomic DNA and total RNA were simultaneously extracted from this material by means of the truXTRAC FFPE extraction kit (Covaris, Inc., Woburn, Mass.), following the manufacturer's instructions with some modifications. Following purification, RNA and DNA were eluted in 30 and 50 µL water, respectively, and yield was determined by the Quant-iT RNA HS Assay and Quantifiler Human DNA Quantification Kits (both from Thermo Fisher Scientific, Waltham, Mass.), as per manufacturer's recommendation. A predefined yield of 10 ng RNA and 30 ng DNA was used as acceptance criteria to ensure adequate library preparation.

Run controls were established and used for library preparation, enrichment and NGS. They included both positive (MuB-DNA, GEX-RNA) and negative (MuB-DNA Negative, GEX-RNA Negative) controls, as well as a no template control (NTC, water). Positive controls provide templates for all targets for qualification and downstream normalization purposes, while negative controls monitor assay specificity. For RNA-seq, the NTC is used to identify the limit of detection at the individual sample level. For DNA-seq, the NTC is used to identify the threshold for false positivity at the run level. The performance characteristics of these five run controls were assessed across multiple weeks to develop thresholds and filters that serve as daily QC parameters on runs and samples.

The assay utilized the Oncomine Immune Response Research Assay (OIRRA) for GEX and the Comprehensive Cancer Panel (CCP) for MuB (Thermo Fisher Scientific). Both these panels use multiplexed gene-specific primer pairs and NGS to amplify nucleic acids extracted from FFPE slides. The OIRRA was adapted to quantify expression of 54 target genes using 10 constitutively expressed housekeeping (HK) genes as normalizers. All 409 cancer-related genes included in the CCP panel were used to estimate MuB from genomic DNA.

OIRRA libraries were prepared using the Ion AmpliSeq targeted sequencing technology (Thermo Fisher Scientific). Briefly, 10 ng RNA was reverse transcribed into cDNA and targets were amplified with a multiplex primer pool. For DNA-seq, CCP libraries were prepared using 30 ng DNA. Barcode adapters were ligated to partially digested amplicons, purified and normalized to 50 pM. Up to 16 equimolar RNA and DNA libraries were pooled prior to enrichment and template preparation using the Ion Chef system (Thermo Fisher Scientific). 200-bp sequencing was performed on the Ion S5XL 540 chip to obtain 1.5-2.5M RNA-seq mapped reads and 100-150×DNA-seq mean depth per sample.

RNA-seq accuracy was evaluated by comparison with qRT-PCR for all reported genes for all samples, and with IHC for CD8A (based on automated image analysis for a subset of 57 samples with adequate material). For orthogonal qRT-PCR analysis, 100 ng RNA was reverse-transcribed, amplified and measured in triplicate by means of the TaqMan Gene Expression Assay monitoring the 54 target and 10 HK genes using the QuantStudio 7 Real-Time PCR System (Applied BioSystems, Foster City, Calif.). For IHC, 5 µm-thick sections from tissue microarrays (TMAs) with three 0.6-mm tissue cores arrayed per tumor were stained with antibodies specific for CD8A (C8/144B, Dako, Agilent Technologies, Santa Clara, Calif.) as per standard procedures, and PD-L1 is run specific to tumor histology (22C3, Dako, or 28-8 Dako, or SP142 Ventana), as per FDA guidelines. Quantitative IHC data on CD8A+ T-cell counts were obtained using the Aperio Scanscope (Aperio Technologies, Inc., Vista, Calif.), based on 20× bright-field optical microscopy. Images were analyzed using eSlide Manager v12.2.1 (Aperio Technologies, Inc.) and the number of positive cells per sqmm for each TMA core was counted. Quantitative IHC expression data for PD-L1 was obtained by trained pathologists interpreting the tumor proportion score (TPS), H-score (HS), and modified H-score (MHS). A minimum of two evaluable cores out of three was required for inclusion in final analysis. Average number of CD8A+ cells per sqmm, TPS, HS, and MHS were derived from each sample upon individual analysis of at least two cores.

Sequencing data were first processed using the Torrent Suite software (v5.2.0) for reference mapping and base calling, during which validation-defined QC specifications for mapped reads, on-target reads, mean read length, mean depth, uniformity, and percent valid reads were used as acceptance criteria. To ensure high quality results, a QC system was developed based on NGS data generated at validation. The QC criteria were established for several metrics at the run, sample, amplicon and base-pair level for each nucleic acid type and run control thresholds, with defined values to accept or reject one or more aspects of sequencing. Likewise, specific QC metrics are monitored over time to detect any potential long-term assay drift. Quality filters are used at the amplicon level to remove counts below the threshold for detection, and at the base-pair level for low-quality variant calls.

RNA-seq absolute reads were generated using Torrent Suite's plugin immuneResponseRNA (v5.2.0.0). For each transcript, absolute read counts from the NTC were considered as the library preparation background and hence were subtracted from absolute read counts of the same transcript of all other samples in the same preparation batch. To allow NGS measurements across runs to be comparable for evaluation and interpretation, background-subtracted read counts were subsequently normalized into normalized reads per million (nRPM) values as follows. Each HK gene background-subtracted reads was compared against a predetermined HK reads per million (RPM) profile. The HK RPM profile was established based on the average RPM of multiple replicates of the GM12878 sample across different sequencing runs of the validation. This produced a fold-change ratio for each HK gene:

$$\text{Ratio of } HK = \frac{\text{Background Subtracted Read Count of } HK}{\text{RPM Profile of } HK}$$

After this, the median value of all HK ratios was used as the normalization ratio for the particular sample:

Normalization Ratio=Median(all HK ratios)

The nRPM of all genes (G) of the particular sample (S) was then calculated as:

$$nRPM_{(S,G)} = \frac{\text{Background subtracted Read Count}_{(S,G)}}{\text{Normalization Ratio}_{(S)}}$$

DNA-seq variant calling was conducted using Ion Torrent Suite software's (v5.2.0) variantCaller (v5.2.0.34) plugin, which requires a minimal minor allele frequency (MAF) of 0.1 and a minimal coverage of 20×. A series of filters were applied to variants that generated the MuB-qualified variant subset meeting following criteria: at least one minor allele reads on both strands; <0.2% MAF in 1,000 genomes, Exome Aggregation Consortium (ExAC), and Exome Sequencing Project (ESP) databases; missense or nonsense; has co-located somatic variants as in Ensembl team's curated database. The count of MuB-qualified variants was further normalized over the number of exonic bases with ≥20× coverage, as reflected in the input BAM file, to generate the normalized MuB score, interpreted as the number of mutations per million exonic bases. High MuB was defined as >2× standard deviation of the mean number of mutations per megabase DNA in a tumor reference population of varying histology.

For RNA-seq, the suitability of FFPE specimens was established by comparing RNA-seq results obtained from FFPE versus matched FF samples. Principal component analysis (PCA) was used to show that different sections obtained from a given FFPE sample do not lead to different RNA-seq results, that potential confounders such as the amount or quality of stroma are well tolerated by the assay, and that testing either multiple foci of a metastatic tumor or the primary lesion has a minimal impact on results (data not shown). For MuB, sensitivity of variant detection was used to evaluate minimal threshold for percent neoplastic nuclei.

To compare RNA-seq with gold-standard Taqman qRT-PCR, nRPM values of target genes were log 2 transformed, which allowed for appropriate comparison with ΔCt values from qRT-PCR measurements. The Pearson product-moment correlation coefficient (R) was then calculated for each gene on log-transformed GEX measurements and ΔCt values. Any gene with poor correlation values (<0.7) was excluded from final reporting. To assess GEX correlation for pre-analytical, analytical and reproducibility studies, the R value for nRPM of 54 target genes was used as part of the variables. R was calculated for FFPE versus unstained sections, FF versus FFPE sections, varying percentage of non-neoplastic tissue content, necrotic tissue content, amount of input RNA (ng), genomic DNA (gDNA) contamination, batch size, linearity of expression, inter-run reproducibility, intra-run reproducibility, inter-operator reproducibility and inter-day reproducibility. Additionally, to demonstrate the linearity in absolute reads for different library dilutions, coefficient of determination (R2) was used. Also, average coefficient of variation (CV) for the nRPM of the 54 target genes was calculated as a measure of dispersion of GEX measurements for various batch sizes.

To assess the correlation of MuB counts to gold standard TCGA whole-exome data, TCGA whole-exome counts were filtered to select genomic regions from the MuB panel. The TCGA variant count mapped to the panel's Browser Extensible Data (BED) file was then correlated with MuB counts using Pearson product-moment correlation. DNA stability was tested using two-tailed Student's t test between the mean MuB values of FFPE versus unstained sections. Average CV was calculated as a measure of variability in MuB measurements for FFPE versus unstained sections. CV was also used to demonstrate the effect of DNA input amount (ng) on MuB measurements.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. A method for analyzing a patient's tumor, the method comprising the steps of:
    determining a qualitative and/or quantitative assessment of tumor infiltrating lymphocytes in a sample from the tumor, comprising determining mRNA expression of a plurality of genes associated with tumor infiltrating lymphocytes;
    determining a qualitative and/or quantitative assessment of T-cell receptor signaling in the sample, comprising determining mRNA expression of a plurality of T-cell receptor signaling genes (TCRS) associated with anti-cancer immune response and/or immunotherapeutic targets;
    determining a qualitative and/or quantitative assessment of mutational burden in the sample, comprising DNA sequencing and analysis of the sample;
    classifying, based on the determined qualitative and/or quantitative assessment of tumor infiltrating lymphocytes, the determined qualitative and/or quantitative assessment of T-cell receptor signaling, and the determined qualitative and/or quantitative assessment of mutational burden, the sample as a responder to a therapy;
    determining a response of the tumor, based on classifying the sample as a responder to a therapy, to one or more possible treatment therapies; and
    administering the determined one or more possible treatment therapies to the patient.

2. The method of claim 1, wherein the treatment is an immune checkpoint blockade therapy for the tumor.

3. The method of claim 2, wherein the immune checkpoint blockade therapy is ipilimumab or a similar drug.

4. The method of claim 1, further comprising the step of correlating the determined classification of the sample with a second classification.

5. The method of claim 4, further comprising the step of determining a response of the tumor, based on the correlation, to one or more possible treatment therapies.

6. The method of claim 1, further comprising the step of determining immunohistochemistry data for the sample, wherein said classifying step is further based on the determined immunohistochemistry data.

7. The method of claim 1, wherein the plurality of genes associated with tumor infiltrating lymphocytes comprises at least CD163, CD2, CD3D, CD3E, CD3G, CD4, CD68, CD8A, CD8B, FOXP3 and CD20.

8. The method of claim 1, wherein the plurality of genes associated with tumor infiltrating lymphocytes consists of CD163, CD2, CD3D, CD3E, CD3G, CD4, CD68, CD8A, CD8B, FOXP3 and CD20.

9. The method of claim 1, wherein the plurality of genes associated with tumor infiltrating lymphocytes, and/or the plurality of T-cell receptor signaling genes associated with anti-cancer immune response and/or immunotherapeutic targets, consists of CD163, CD2, CD3D, CD3E, CD3G, CD4, CD68, CD8A, CD8B, FOXP3 and CD20.

10. The method of claim 1, wherein the plurality of T-cell receptor signaling genes associated with anti-cancer immune response and/or immunotherapeutic targets comprises the 43 TCRS genes listed in

TABLE 1

Genes Utilized for an Embodiment of the 54 Gene Model

| TILs Genes (11) | TCRS Genes (43) | | | |
|---|---|---|---|---|
| CD163 | ADORA2A | CD40LG | TIM3 | PD-L2 |
| CD2 | BTLA | CD80 (B7-1) | ICOS | STAT1 |
| CD3D | VISTA (B7-H5) | CD86 (B7-2) | ICOSLG | TBX21 |
| CD3E | CCL2 | CSF1R | IDO1 | TGFB1 |
| CD3G | CCR2 | CTLA4 | IFNG | TNF |
| CD4 | SLAMF4 | CXCL10 | IL10 | TNFRSF14 |
| CD68 | CD27 (TNFRSF27) | CXCR6 | IL1B | GITR |
| CD8A | PD-L1 | DDX58 | KLRD1 | OX40 |
| CD8B | CD28 | ENTPD1 | LAG3 | CD137 |
| FOXP3 | CD38 | GATA3 | MX1 | OX-40L |
| CD20 | CD40 | GZMB | PD-1. | |

11. The method of claim 1, wherein the plurality of T-cell receptor signaling genes associated with anti-cancer immune response and/or immunotherapeutic targets consists of the 43 TCRS genes listed in

TABLE 1

Genes Utilized for an Embodiment of the 54 Gene Model

| TILs Genes (11) | TCRS Genes (43) | | | |
|---|---|---|---|---|
| CD163 | ADORA2A | CD40LG | TIM3 | PD-L2 |
| CD2 | BTLA | CD80 (B7-1) | ICOS | STAT1 |
| CD3D | VISTA (B7-H5) | CD86 (B7-2) | ICOSLG | TBX21 |
| CD3E | CCL2 | CSF1R | IDO1 | TGFB1 |
| CD3G | CCR2 | CTLA4 | IFNG | TNF |
| CD4 | SLAMF4 | CXCL10 | IL10 | TNFRSF14 |
| CD68 | CD27 (TNFRSF27) | CXCR6 | IL1B | GITR |
| CD8A | PD-L1 | DDX58 | KLRD1 | OX40 |
| CD8B | CD28 | ENTPD1 | LAG3 | CD137 |
| FOXP3 | CD38 | GATA3 | MX1 | OX-40L |
| CD20 | CD40 | GZMB | PD-1. | |

12. The method of claim 1, wherein the plurality of T-cell receptor signaling genes associated with anti-cancer immune response and/or immunotherapeutic targets, and/or the plurality of genes associated with tumor infiltrating lymphocytes, comprises at least some of the genes listed in

TABLE 1

Genes Utilized for an Embodiment of the 54 Gene Model

| TILs Genes (11) | TCRS Genes (43) | | | |
|---|---|---|---|---|
| CD163 | ADORA2A | CD40LG | TIM3 | PD-L2 |
| CD2 | BTLA | CD80 (B7-1) | ICOS | STAT1 |
| CD3D | VISTA (B7-H5) | CD86 (B7-2) | ICOSLG | TBX21 |
| CD3E | CCL2 | CSF1R | IDO1 | TGFB1 |
| CD3G | CCR2 | CTLA4 | IFNG | TNF |
| CD4 | SLAMF4 | CXCL10 | IL10 | TNFRSF14 |
| CD68 | CD27 (TNFRSF27) | CXCR6 | IL1B | GITR |
| CD8A | PD-L1 | DDX58 | KLRD1 | OX40 |
| CD8B | CD28 | ENTPD1 | LAG3 | CD137 |
| FOXP3 | CD38 | GATA3 | MX1 | OX-40L |
| CD20 | CD40 | GZMB | PD-1. | |

13. The method of claim 1, wherein the plurality of T-cell receptor signaling genes associated with anti-cancer immune response and/or immunotherapeutic targets, and/or the plurality of genes associated with tumor infiltrating lymphocytes, comprises the genes listed in

TABLE 1

Genes Utilized for an Embodiment of the 54 Gene Model

TILs Genes (11)

TCRS Genes (43)

| CD163 | ADORA2A | CD40LG | TIM3 | PD-L2 |
|---|---|---|---|---|
| CD2 | BTLA | CD80 (B7-1) | ICOS | STAT1 |
| CD3D | VISTA (B7-H5) | CD86 (B7-2) | ICOSLG | TBX21 |
| CD3E | CCL2 | CSF1R | IDO1 | TGFB1 |
| CD3G | CCR2 | CTLA4 | IFNG | TNF |
| CD4 | SLAMF4 | CXCL10 | IL10 | TNFRSF14 |
| CD68 | CD27 (TNFRSF27) | CXCR6 | IL1B | GITR |
| CD8A | PD-L1 | DDX58 | KLRD1 | OX40 |
| CD8B | CD28 | ENTPD1 | LAG3 | CD137 |
| FOXP3 | CD38 | GATA3 | MX1 | OX-40L |
| CD20 | CD40 | GZMB | PD-1. | |

14. The method of claim 1, wherein the DNA sequencing and analysis of the sample comprises whole or partial exome sequencing.

15. The method of claim 1, wherein the DNA sequencing and analysis of the sample comprises whole genome sequencing.

16. The method of claim 1, wherein the mutational burden in the sample is a number of mutations per megabase of DNA.

17. The method of claim 16, wherein the determined mutational burden is classified based on comparison to a reference population.

18. The method of claim 17, wherein the determined mutational burden is classified as one of: (1) very high; (2) high; (3) intermediate; (4) low; and (5) very low based on said comparison.

19. The method of claim 1, wherein classifying the sample as a responder to a therapy comprises a Bayesian Model Averaging of the determined qualitative and/or quantitative assessment of tumor infiltrating lymphocytes, the determined qualitative and/or quantitative assessment of T-cell receptor signaling, and the determined qualitative and/or quantitative assessment of mutational burden.

* * * * *